US011738336B2

United States Patent
Braganca et al.

(10) Patent No.: US 11,738,336 B2
(45) Date of Patent: Aug. 29, 2023

(54) SPIN TORQUE OSCILLATOR (STO) SENSORS USED IN NUCLEIC ACID SEQUENCING ARRAYS AND DETECTION SCHEMES FOR NUCLEIC ACID SEQUENCING

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 466 days.

(21) Appl. No.: 16/791,759

(22) Filed: Feb. 14, 2020

(65) Prior Publication Data
US 2020/0324283 A1    Oct. 15, 2020

Related U.S. Application Data

(60) Provisional application No. 62/833,161, filed on Apr. 12, 2019.

(51) Int. Cl.
*B01L 3/00*        (2006.01)
*H03B 15/00*     (2006.01)
(Continued)

(52) U.S. Cl.
CPC .............. *B01L 3/502* (2013.01); *G01N 24/00* (2013.01); *G01N 27/72* (2013.01); *H01F 10/329* (2013.01);
(Continued)

(58) Field of Classification Search
CPC ............. B01L 3/502; B01L 2300/0663; B01L 2400/043; B01L 3/5027; G01N 24/00;
(Continued)

(56) References Cited

U.S. PATENT DOCUMENTS 5,302,509 A    4/1994   Cheeseman
6,037,167 A    3/2000   Adelman et al.
(Continued)

FOREIGN PATENT DOCUMENTS

CN    102928596 A    2/2013
CN    103885000 A    6/2014
(Continued)

OTHER PUBLICATIONS

U.S. Appl. No. 62/833,130, filed Apr. 12, 2019, Yann Astier.
(Continued)

*Primary Examiner* — Elizabeth A Robinson
*Assistant Examiner* — Jean Caraballo-Leon

(57) ABSTRACT

Disclosed herein is a detection device comprising sensors with spin torque oscillators (STOs), at least one fluidic channel configured to receive molecules to be detected, and detection circuitry coupled to the sensors. At least some of the molecules to be detected are labeled by magnetic nanoparticles (MNPs). The presence of one or more MNPs in the vicinity of a STO subjected to a bias current changes the oscillation frequency of the STO. The sensors are encapsulated by a material, such as an insulator, separating the sensors from the at least one fluidic channel. A surface of the material provides binding sites for the molecules to be detected. The detection circuitry is configured to detect changes in the oscillation frequencies of the sensors in response to presence or absence of one or more MNPs coupled to one or more binding sites associated with the sensors.

48 Claims, 19 Drawing Sheets

(51) Int. Cl.
   *H01F 10/32*      (2006.01)
   *C12Q 1/6869*     (2018.01)
   *G01N 27/72*      (2006.01)
   *G01N 24/00*      (2006.01)
   *G01R 33/12*      (2006.01)

(52) U.S. Cl.
   CPC ..... *H01F 10/3259* (2013.01); *H01F 10/3286* (2013.01); *H03B 15/006* (2013.01); *B01L 2300/0663* (2013.01); *B01L 2400/043* (2013.01); *G01R 33/1284* (2013.01)

(58) Field of Classification Search
   CPC . G01N 27/72; H01F 10/3259; H01F 10/3286; H01F 10/329; H01F 10/3254; H03B 15/006; G01R 33/1284; G01R 33/0029; G01R 33/0041; G01R 33/098; G01R 33/1269; C12Q 1/6869
   See application file for complete search history.

(56) References Cited

U.S. PATENT DOCUMENTS

| | | | |
|---|---|---|---|
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,435,791 B2 | 9/2016 | Acosta et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 10,203,379 B2 | 2/2019 | Wang et al. |
| 10,260,095 B2 | 4/2019 | Esfandyarpour et al. |
| 10,591,440 B2 | 3/2020 | Astier et al. |
| 2004/0043479 A1 | 3/2004 | Briscoe et al. |
| 2004/0219695 A1 | 11/2004 | Fox |
| 2005/0054081 A1 | 3/2005 | Hassard et al. |
| 2005/0118102 A1 | 6/2005 | Xiang et al. |
| 2007/0224700 A1 | 9/2007 | Masters |
| 2007/0264159 A1 | 11/2007 | Graham et al. |
| 2008/0218165 A1 | 9/2008 | Kahlman et al. |
| 2008/0241569 A1 | 10/2008 | Qin et al. |
| 2009/0066318 A1 | 3/2009 | Kahlman et al. |
| 2009/0148857 A1 | 6/2009 | Srivastava et al. |
| 2009/0206832 A1 | 8/2009 | Kahlman et al. |
| 2009/0208957 A1 | 8/2009 | Korlach et al. |
| 2010/0039105 A1 | 2/2010 | Ryan et al. |
| 2010/0111768 A1 | 5/2010 | Banerjee et al. |
| 2010/0194386 A1 | 8/2010 | Prins et al. |
| 2010/0207631 A1 | 8/2010 | McDowell |
| 2010/0231214 A1 | 9/2010 | Zhou |
| 2011/0223612 A1 | 9/2011 | Wang et al. |
| 2012/0295262 A1 | 11/2012 | Ronaghi et al. |
| 2013/0148223 A1 | 6/2013 | Braganca et al. |
| 2014/0008281 A1 | 1/2014 | Ramanathan et al. |
| 2014/0139214 A1 | 5/2014 | Park et al. |
| 2014/0292318 A1 | 10/2014 | Wang et al. |
| 2016/0131613 A1 | 5/2016 | Jayant et al. |
| 2017/0304825 A1 | 10/2017 | Issadore et al. |
| 2018/0074016 A1 | 3/2018 | Chen et al. |
| 2018/0100190 A1 | 4/2018 | Esfandyarpour et al. |
| 2018/0128822 A1 | 5/2018 | Wang et al. |
| 2018/0237850 A1 | 8/2018 | Mandell et al. |
| 2018/0284200 A1 | 10/2018 | Chen et al. |
| 2019/0032114 A1 | 1/2019 | Trivedi |
| 2019/0170680 A1 | 6/2019 | Sikora et al. |
| 2019/0390267 A1 | 12/2019 | Astier et al. |
| 2021/0047681 A1 | 2/2021 | Mendonsa et al. |
| 2021/0047682 A1 | 2/2021 | Mendonsa et al. |

FOREIGN PATENT DOCUMENTS

| | | |
|---|---|---|
| CN | 107873060 A | 4/2018 |
| CN | 108138229 A | 6/2018 |
| CN | 107051597 B | 8/2019 |
| EP | 1544310 A2 | 6/2005 |
| EP | 2674264 A2 | 12/2013 |
| EP | 3208627 A1 | 8/2017 |
| ES | 2674264 | 6/2018 |
| WO | 2005047864 A3 | 9/2005 |
| WO | 2005124345 A3 | 4/2006 |
| WO | 2007105141 A2 | 9/2007 |
| WO | 2015031691 A1 | 3/2015 |
| WO | 2016183218 A1 | 11/2016 |
| WO | 2017030999 A1 | 2/2017 |
| WO | 2017061129 A1 | 4/2017 |
| WO | 2018017884 A1 | 1/2018 |
| WO | 2018186539 A1 | 10/2018 |
| WO | 2019068204 A1 | 4/2019 |
| WO | 2020210370 A1 | 10/2020 |

OTHER PUBLICATIONS

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Dell Biology, Dec. 2015, vol. 25, No. 12, pp. 730-748.

B. N. Engel, et al., "A4-Mb Toggle MRAM Based on a Novel Bit and Switching Method," IEEE Transactions on Magnetics, vol. 41, No. 1, Jan. 2005.

C. Chappert et al., "The emergence of spin electronics in data storage," Nature Materials, Dec. 2007.

C.H. Smith et al., "High-resolution giant magnetoresistance on-chip arrays for magnetic imaging," Journal of Applied Physics 93, 6864 (2003).

(56) References Cited

OTHER PUBLICATIONS

D. Ross et al., "Temperature Measurement in Microfluidic Systems Using a Temperature-Dependent Fluorescent Dye," Anal. Chem. 2001, 73, 17,4117-4123, Jul. 24, 2001.
ePHOTOzine.com, "Complete Guide to Image Sensor Pixel Size," Aug. 2, 2016, available at https://www.ephotozine.com/article/complete-guide-to-image-sensor-pixel-size-29652.
F. Grasset et al., "Synthesis, magnetic properties, surface modification and cytotoxicity evaluation of Y3Fe5-xAlxO12 (0?x?2) garnet submicron particles for biomedical applications," Journal of Magnetism and Magnetic Materials, vol. 234, Issue 3, Sep. 2001, pp. 409-418.
F. Menges et al., "Temperature mapping of operating nanoscale devices by scanning probe thermometry," Nature Communications, 7:10874, Mar. 3, 2016.
Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).
Illumina, "NovaSeq 6000 Sequencing System," 2019, available at https://www.illumina.com/systems/sequencing-platforms/novaseq.html.
International Search Report from PCT App. No. PCT/US2016/046888, dated Oct. 26, 2016.
J. Sakakibara et al., "Measurements of thermally stratified pipe flow using image-processing techniques," Experiments in Fluids, Dec. 1993, vol. 16, Issue 2, pp. 82-96.
John PEARCE, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.
Lin Gui and Carolyn L. Ren, "Temperature measurement in microfluidic chips using photobleaching of a fluorescent thin film," Applied Physics Letters 92, 024102, 2008.
M. Aslam et al., "Silica encapsulation and magnetic properties of FePt nanoparticles," Journal of Colloid and Interface Science 290 (2005) 444-449.
M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.
M.T. Tlili et al., "Magnetic, Electrical Properties and Spin-Glass Effect of Substitution of Ca for Pr in Ca2-xPrxMnO4 Compounds," The Open Surface Science Journal, 2009, vol. 1, pp. 54-58.
N. X. Phuc, et al., "Tuning of the Curie Temperature in La1-xSrxMn1-yTiyO3" J. Korean Phy. Soc., vol. 52, No. 5, May 2008, pp. 1492-1495.
N.R. Patil et al., "Effect of temperature on the fluorescence emission of ENCTTTC in different nonpolar solvents," Can. J. Phys. 91: 971-975 (2013).
R. Giri, "Temperature effect study upon the fluorescence emission of substituted coumarins," Spectrochimica Acta Part A: Molecular Spectroscopy, vol. 48, Issue 6, Jun. 1992, p. 843-848.
S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.
S.I. Kiselev et al., "Microwave oscillations of a nanomagnet driven by a spin-polarized current," Nature 425, pp. 380-383, 2003.
T. Nagasawa et al., "Delay detection of frequency modulation signal from a spin-torque oscillator under a nanosecond-pulsed magnetic field," Journal of Applied Physics, vol. 111, 07C908 (2012).
W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.
Weifeng Shen et al., "Detection of DNA labeled with magnetic nanoparticles using MgO-based magnetic tunnel junction sensors," Journal of Applied Physics 103, 07A306 (2008).
International Search Report and Written Opinion from PCT Application No. PCT/US2021/021274 (filed Mar. 7, 2021), dated Sep. 28, 2021.
International Search Report and Written Opinion from PCT Application No. PCT/US2021/028263 (filed Apr. 21, 2021), dated Aug. 26, 2021.
International Search Report and Written Opinion from PCT Application No. PCT/US2021/040767 (filed Jul. 8, 2021), dated Oct. 25, 2021.
E. du Trémolet de Lacheisserie, D. Gignoux, and M. Schlenker (editors), Magnetism: Materials and Applications, vol. 2. Springer, 2005.
E. Hall, "On a New Action of the Magnet on Electric Currents," American Journal of Mathematics, vol. 2, 287, 1879.
G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.
International Search Report and Written Opinion from PCT Application No. PCT /US2020!027290 (filed Apr. 8, 2020), dated Jun. 25, 2020.
International Search Report and Written Opinion from PCT Application No. PCT/US2019/068131 (filed Dec. 20, 2019), dated Apr. 1, 2020.
International Search Report and Written Opinion from PCT Application No. PCT/US2019/068535 (filed Dec. 26, 2019), dated Apr. 26, 2020.
International Search Report and Written Opinion from PCT Application No. PCT/US2020/014707 (filed Jan. 23, 2020), dated May 11, 2020.
International Search Report and Written Opinion from PCT Application No. PCT/US2020/021776 (filed Mar. 9, 2020), dated Sep. 1, 2020.
International Search Report and Written Opinion from PCT Application No. PCT/US2020/023069 (filed Mar. 17, 2020), dated Jul. 20, 2020.
International Search Report and Written Opinion from PCT Application No. PCT/US2020/023078 (filed Mar. 17, 2020), dated Jul. 19, 2020.
International Search Report and Written Opinion from PCT Application No. PCT/US2020/035915 (filed Jun. 3, 2020), dated Aug. 26, 2020.
J. C. Slonczewski, "Current-driven excitation of magnetic multilayers," Journal of Magnetism and Magnetic Materials, vol. 159, L1, 1996.
L. Berger, "Emission of spin waves by a magnetic multilayer traversed by a current," Physical Review B, vol. 54, 9353, 1996.
Lany, M., G. Boero, and R. S. Popovic. "Superparamagnetic microbead inductive detector". Review of scientific instruments 76.8 (2005): 084301.
Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.
M. Díaz-Michelena, "Small Magnetic Sensors for Space Applications," Sensors, vol. 9, 2271, 2009.
Michael L. Metzker, "Sequencing Technologies—the Next Generation," Nature Rev. Genet. 11: 31-46 (2009).
Miller, M. M., et al. "A DNA array sensor utilizing magnetic microbeads and magnetoelectronic detection". Journal of Magnetism and Magnetic Materials 225.1-2 (2001): 138 144.
P. Anderson, J. Rowell, "Probable Observation of the Josephson Superconducting Tunneling Effect," Physical Review Letters, vol. 10, 230, 1963.
P. M. Braganca, B. A. Gurney, B. A. Wilson, J. A. Katine, S. Maat and J. R. Childress, "Nanoscale magnetic field Tetection using a spin torque oscillator," Nanotechnology, vol. 21, 235202, 2010.
P. Namdari, H. Daraee, and A. Eatemadi, "Recent Advances in Silicon Nanowire Biosensors: Synthesis Methods, Properties and Applications", Nanoscale Research Letters, vol. 11, 406, 2016.
Quynh, L. K., et al. Detection of magnetic nanoparticles using simple AMR sensors in Wheatstone bridge. Journal of Science: Advanced Materials and Devices, 2016, 1.1: 98-102.

(56) References Cited

OTHER PUBLICATIONS

R. C. Jaklevic, J. Lambe, A. H. Silver & J. E. Mercereau, "Quantum Interference Effects in Josephson Tunneling," Physical Review Letters, vol. 12, 159, 1964.

R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions on Magnetics, vol. 48, 1758, 2012.

Rabehi, A., Electromagnetic microsystem for the detection of magnetic nanoparticles in a microfluidic structure for mmunoassays (Doctoral dissertation). Jan. 29, 2020.

Rauwerdink, A. M., Giustini, A. J., & Weaver, J. B. (2010). Simultaneous quantification of multiple magnetic nanoparticles. Nanotechnology, 21(45), 455101.

Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.

Srimani T et al., "High Sensitivity Biosensor using Injection Locked Spin Torque Nano-Oscillators," arXiv: 1511.09072, Nov. 2015.

Tang, C., He, Z., Liu, H., Xu, Y., Huang, H., Yang, G., . . . & Chen, Z. (2020). Application of magnetic nanoparticles in nucleic acid detection Journal of Nanobiotechnology, 18, 1-19 Apr. 21, 2020.

Wang, W., & Jiang, Z., "Thermally assisted magnetic tunneling junction for biosensing applications," IEEE Transactions on Magnetics, 43(6), 2406-2408, Jun. 30, 2007.

Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).

Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.

Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.

Daschiel et al. The holy grail of microfluidics: sub-laminar drag by layout of periodically embedded microgrooves (2013) MicrofluidNanofluid 15, 675-687.

Mao et al. A Microfluidic Device with a Linear Temperature Gradient for Parallel and Combinatorial Measurements (2002) J AmChem Soc 124, 4432-4435.

Qiu et al. Instrument-free point-of-care molecular diagnosis of H 1 N 1 based on microfluidic convective PCR (2017) Sensors andActuators B: Chemical 243, 738-744.

Mohamad, O. and Ho, W. S., "The Next Generation Sequencing Technologies," Jilid 18 No. 1 &2/ISSN 1394-5750 Jan. & Jul. 2011.

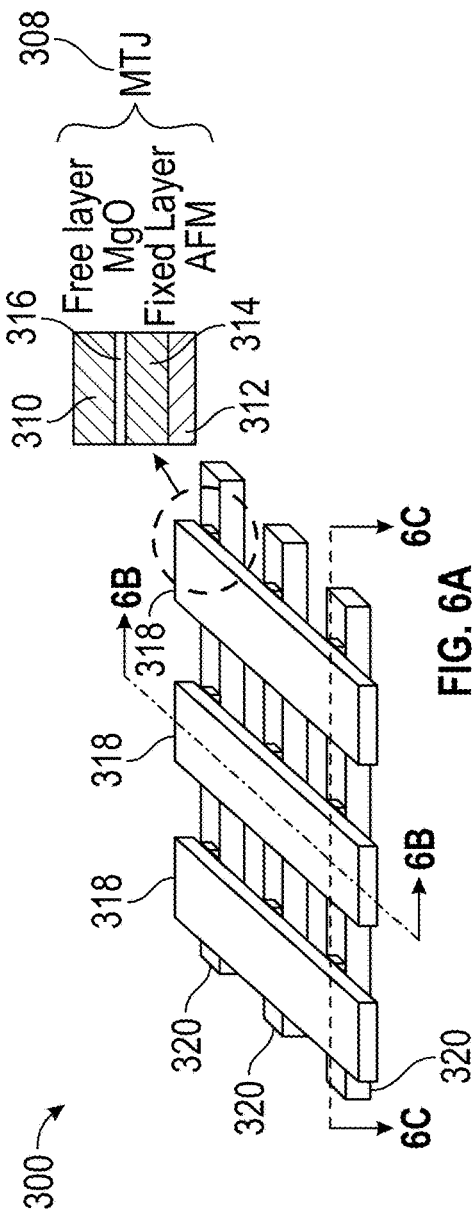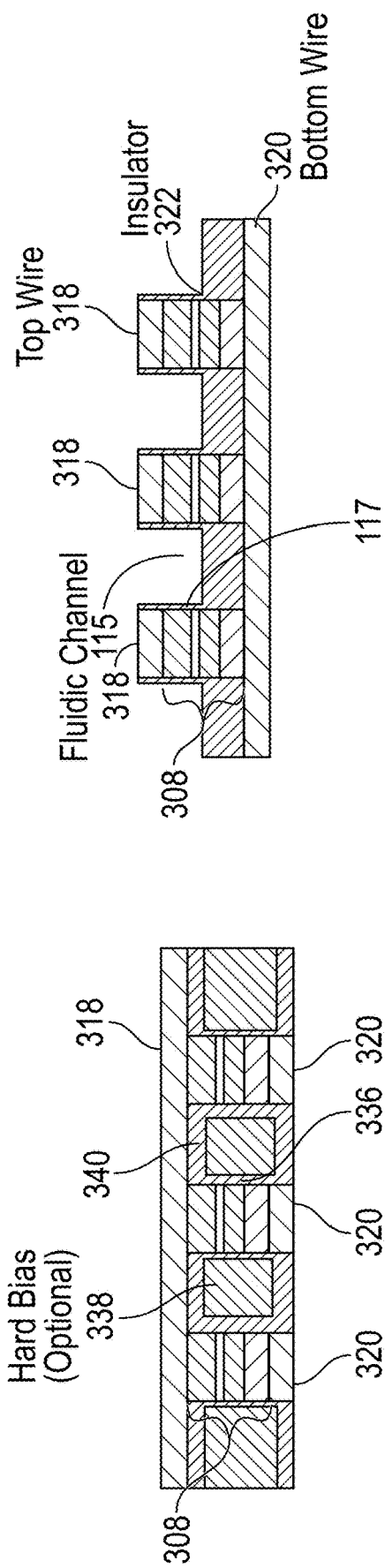

SPIN TORQUE OSCILLATOR (STO) SENSORS USED IN NUCLEIC ACID SEQUENCING ARRAYS AND DETECTION SCHEMES FOR NUCLEIC ACID SEQUENCING

CROSS-REFERENCE TO RELATED APPLICATIONS

This application claims the benefit of and hereby incorporates by reference, for all purposes, the entirety of the contents of U.S. Provisional Application No. 62/833,161, filed Apr. 12, 2019 and entitled "SPIN TORQUE OSCILLATOR (STO) SENSORS USED IN NUCLEIC ACID SEQUENCING ARRAYS AND DETECTION SCHEMES FOR NUCLEIC ACID SEQUENCING."

BACKGROUND

Field of the Disclosure

Embodiments of the present disclosure generally relate to magnetoresistive (MR) sensor arrays for detection of molecules coupled to magnetic nanoparticles (MNPs), such as for nucleic acid sequencing such as deoxyribonucleic acid (DNA) sequencing, and methods of using such MR sensor arrays for molecule detection.

Description of the Related Art

Current state-of-the-art sequencing systems are based on fluorescence signal detection and provide throughputs of 20 billion reads per run (https://www.illumina.com/systems/sequencing-platforms/novaseq.html). Achieving such performance, however, can require large-area flow cells, high-precision free-space imaging optics, and expensive high-power lasers to generate sufficient fluorescence signals for successful base detection.

One type of nucleic acid sequencing used for DNA sequencing is known as "sequencing by synthesis" (SBS). SBS involves binding of primer-hybridized template DNA, incorporation of a deoxynucleoside triphosphate (dNTP), and detection of incorporated dNTP. Gradual increases in SBS throughput have been accomplished in two ways, the first being an outward scaling, where the size and the number of flow cells in the sequencers is increased. This approach increases both the cost of reagents and the price of the sequencing system, as more high-power lasers and high-precision nano-positioners must be employed. The second approach involves inward scaling, where the density of DNA testing sites is increased so that the total number of sequenced DNA strands in a fixed-size flow cell is higher. To accomplish inward scaling, increasingly higher numerical aperture (NA) lenses must be employed to distinguish the signal from neighboring fluorophores as the spacing between them decreases. However, this approach cannot be implemented indefinitely, as the Rayleigh criterion puts the distance between resolvable light point sources at $0.61\lambda/NA$, constraining the minimum distance between two sequenced DNA strands to be no smaller than approximately 400 nm. Similar resolution limits apply to sequencing directly on top of imaging arrays (similar to cell phone cameras), where the smallest pixel size achieved so far is approximately 1 μm (https://www.ephotozine.com/article/complete-guide-to-image-sensor-pixel-size-29652).

The Rayleigh criterion currently represents the fundamental limitation for inward scaling of optical SBS systems, which can only be overcome by applying super-resolution imaging techniques (see A. M. Sydor, K. J. Czymmek, E. M. Puchner, and V. Mannella, "Super-Resolution Microscopy: From Single Molecules to Supramolecular Assemblies," Special Issue: Quantitative Cell Biology, Vol. 25, 730, 2015) and has not yet been achieved in highly multiplexed systems. Hence, increasing throughput and decreasing cost of optical SBS sequencers has been slow due to the need to build bigger flow cells and implement more expensive optical scanning and imaging systems.

Therefore, there is a need for new and improved apparatuses for and methods of detecting the presence of molecules such as nucleic acids that overcome the limitations of conventional apparatuses and methods.

SUMMARY

This summary represents non-limiting embodiments of the disclosure.

Disclosed herein are apparatuses and methods of using magnetic particles and magnetic sensors comprising spin torque oscillators (STDs) to perform molecule detection, such as for nucleic acid sequencing (e.g., DNA sequencing using SBS chemistry methods).

Disclosed herein are improved detection devices, systems, and methods that use magnetic nanoparticles (MNPs) to allow molecules (e.g., nucleic acids) to be identified. The disclosures herein include embodiments having sensors with STOs that allow for detection of characteristics indicating the presence or absence of MNPs near sensors. Also disclosed herein are detection method embodiments that can be used to detect (e.g., measure or obtain) characteristics or changes in characteristics generated by the sensors indicative of the presence or absence of MNPs (e.g., in response to a magnetic field generated, or not generated, by a magnetic nanoparticle label). For example, devices and methods may determine whether a sensor is or is not generating a signal having a frequency at a particular frequency or within a specified range of frequencies, and, based thereon, determine whether one or more MNPs are being detected by the sensor. As another example, devices and methods may detect a change in a signal generated, or not generated, by a sensor and, based thereon, determine whether one or more MNPs are being detected by the sensor.

In some embodiments, a detection device comprises a sensor comprising a STO, at least one fluidic channel configured to receive molecules to be detected, wherein at least some of the molecules to be detected are labeled by MNPs, and detection circuitry coupled to the sensor, wherein the sensor is encapsulated by a material separating the sensor from the at least one fluidic channel, a surface of the material providing binding sites for the molecules to be detected, and the detection circuitry is configured to detect presence or absence of magnetization oscillations of the STO in a specified frequency band in response to presence or absence of at least one MNP coupled to one or more binding sites associated with the sensor. In some embodiments, the at least one MNP is superparamagnetic or ferromagnetic. The detection circuitry may include analog components (e.g., amplifiers, mixers, envelope detectors, etc.), digital components (e.g., digital signal processors or any other type of processor, etc.), components that convert signals between the analog and digital domains (e.g., analog-to-digital converters, etc.), or a combination of these components.

In some embodiments, the detection circuitry is configured to detect the presence or absence of the magnetization oscillations of the STO in the specified frequency band by, in part, applying a DC current to the STO.

In some embodiments, a magnetization of the STO is configured to oscillate in the specified frequency band in the absence of the at least one MNP and to fail to oscillate in the specified frequency band in the presence of the at least one MNP. In other embodiments, a magnetization of the STO is configured to oscillate in the specified frequency band in the presence of the at least one MNP and to fail to oscillate in the specified frequency band in the absence of the at least one MNP.

In some embodiments, a magnetization of the STO is configured to oscillate in the specified frequency band in the absence of the at least one MNP and to oscillate in a different frequency band in the presence of the at least one MNP, the different frequency band being disjoint from the specified frequency band. In other embodiments, a magnetization of the STO is configured to oscillate in the specified frequency band in the presence of the at least one MNP and to oscillate in a different frequency band in the absence of the at least one MNP, the different frequency band being disjoint from the specified frequency band.

In some embodiments, the detection circuitry comprises a super-heterodyne detection circuit. In some such embodiments, the super-heterodyne detection circuit comprises a reference oscillator configured to generate a reference signal, and a mixer coupled to the STO, wherein the mixer is configured to mix a signal output from the STO with the reference signal to produce an output signal for processing. In some embodiments having a reference oscillator, a frequency of the reference signal is substantially equal to an expected oscillation frequency of the STO, the expected oscillation frequency being within the specified frequency band. In some embodiments, a frequency of the reference signal is selectable, and the detection circuitry is further configured to select the frequency of the reference signal to substantially match an expected oscillation frequency of the STO in the presence of the at least one MNP. In some embodiments, a frequency of the reference signal is selectable, and the detection circuitry is further configured to select the frequency of the reference signal to substantially match an expected oscillation frequency of the STO in the absence of the at least one MNP.

In some embodiments, the reference oscillator is a first reference oscillator, and the reference signal is a first reference signal at a first frequency that is substantially equal to an expected oscillation frequency of the STO in response to presence of one or more MNPs of a first MNP type, and the super-heterodyne circuit further comprises a second reference oscillator configured to generate a second reference signal at a second frequency, the second frequency being substantially equal to an expected oscillation frequency of the STO in response to the presence of one or more MNPs of a second type, and a switch coupled to a first input of the mixer and configured to couple either the first reference oscillator or the second reference oscillator to the first input of the mixer.

In some embodiments, the detection circuitry further comprises a radio-frequency (RF) amplifier, a filter coupled to and disposed between the STO and an input of the RF amplifier, and a diode or envelope detector coupled to an output of the mixer. In some such embodiments, the RF amplifier is coupled to and disposed between an output of the filter and an input to the mixer. In some such embodiments, the filter is a high-pass filter or a band-pass filter. In some embodiments, the filter is a first filter, and the detection circuitry further comprises a second filter coupled to the output of the mixer, and an additional amplifier coupled to and disposed between an output of the second filter and an input of the diode or envelope detector. In some such embodiments, the second filter is a low-pass filter or a band-pass filter.

In some embodiments, the detection circuitry comprises a reference oscillator coupled to the STO, a processor (e.g., a digital signal processor (DSP)), an analog-to-digital converter (ADC) coupled to an input of the processor, and a low-pass or band-pass filter coupled to an input of the ADC and configured to filter a signal output from the STO and the reference oscillator to generate a signal to be processed by the ADC and the processor. In some such embodiments, the sensor is a first sensor and the STO is a first STO, and the detection device further comprises a second sensor comprising a second STO, the second sensor being encapsulated by the material separating the second sensor from the at least one fluidic channel. In some such embodiments, the detection circuitry is further configured to detect presence or absence of magnetization oscillations of the second STO in the specified frequency band in response to presence of absence of at least one MNP coupled to one or more binding sites associated with the second sensor, and the reference oscillator is also coupled to the second STO.

In some embodiments, the detection circuitry comprises a direct radio-frequency RF ADC, a digital signal processor coupled to an output of the direct RF ADC, and a high-pass or band-pass filter disposed between and coupled to the STO and an input of the direct RF ADC.

In some embodiments, the detection circuitry comprises an amplifier coupled to the STO, an ADC coupled to an output of the amplifier, and a processor (e.g., a DSP) coupled to an output of the ADC. In some such embodiments, the processor is configured to execute machine-executable instructions, that, when executed, cause the processor to identify the presence of the magnetization oscillations of the STO within the specified frequency band. In some embodiments, the detection circuitry further comprises one or more of (a) a high-pass filter disposed between the STO and the amplifier, (b) a band-pass filter disposed between the STO and the amplifier, (c) a mixer having first and second inputs and an output, the first input being coupled to the output of the amplifier, the second input being coupled to an output of a reference oscillator, and the output of the mixer being coupled to an input of the ADC, (d) a low-pass filter disposed between the output of the amplifier and the input of the ADC, or (e) a band-pass filter disposed between the output of the amplifier and the input of the ADC.

In some embodiments including a processor and an ADC, the processor is configured to execute machine-executable instructions that, when executed, cause the DSP to receive, from the ADC, samples of a signal generated by the STO, apply a Fourier transform to the samples, and determine whether a result of the Fourier transform indicates the presence or absence of magnetization oscillations of the STO in the specified frequency band in order to detect the presence or absence of magnetization oscillations of the STO in the specified frequency band.

In some embodiments, the detection circuitry comprises a processor (e.g., a DSP) and an ADC disposed between the STO and the processor. In some such embodiments, the ADC is configured to provide samples of a signal generated by the STO to the processor, and the processor is configured to execute machine-executable instructions that, when executed, cause the processor to perform a frequency-domain analysis of the samples to detect the presence or absence of magnetization oscillations of the STO in the specified frequency band.

In some embodiments, the STO comprises a pinned layer, a free layer, and a spacer layer disposed between the pinned layer and the free layer. In some such embodiments, the pinned layer comprises one or more ferromagnetic (FM) layers. In some embodiments, the one or more FM layers are first one or more FM layers, and the free layer comprises second one or more FM layers. In some embodiments, the spacer layer comprises an insulating layer or a metal layer. In some embodiments, at equilibrium, a magnetic moment of the free layer is oriented substantially co-linearly with a magnetic moment of the pinned layer. In some embodiments, at equilibrium, a magnetic moment of the free layer is oriented substantially parallel to or anti-parallel to a magnetic moment of the pinned layer. In some embodiments, at equilibrium, a magnetic moment of the free layer is oriented at an angle to a magnetic moment of the pinned layer, wherein the angle is between approximately 20 degrees and approximately 60 degrees.

Also disclosed herein is a method of sequencing nucleic acid using a detection device comprising a plurality of STOs and at least one fluidic channel. In some embodiments, the method comprises labeling a nucleotide precursor with a MNP, adding the labeled nucleotide precursor to the fluidic channel of the detection device, determining whether at least one of the plurality of STOs is generating a signal, and based at least in part on the determination of whether the at least one of the plurality of STOs is generating the signal, determining whether the labeled nucleotide precursor has been detected. In some embodiments, determining whether the at least one of the plurality of STOs is generating the signal comprises detecting a presence or absence of a signal at an output of a super-heterodyne circuit coupled to the at least one of the plurality of STOs. In some embodiments, determining whether at least one of the plurality of STOs is generating a signal comprises determining whether at least one of the plurality of STOs is generating a signal within a specified frequency band.

In some embodiments, the method further comprises binding at least one nucleic acid strand to a binding site in the fluidic channel, and adding, to the fluidic channel, an extendable primer and a plurality of molecules of nucleic acid polymerase before adding the labeled nucleotide precursor to the fluidic channel of the detection device.

In some embodiments, the method further comprises recording (a) an identity of the nucleotide precursor, or (b) an identity of a base complementary to the labeled nucleotide precursor in response to determining that the labeled nucleotide precursor has been detected.

In some embodiments, a method of sequencing nucleic acid using a detection device comprising a plurality of STOs and at least one fluidic channel comprises labeling a first nucleotide precursor with a first MNP type, the first MNP type selected to cause a magnetization of each of the plurality of STOs to oscillate at a first frequency, labeling a second nucleotide precursor with a second MNP type, the second MNP type selected to cause the magnetization of each of the plurality of STOs to oscillate at a second frequency, adding the labeled first and second nucleotide precursors to the fluidic channel of the detection device, detecting a frequency of a signal generated by at least one of the plurality of STOs, determining whether the frequency of the signal generated by the at least one of the plurality of the STOs matches the first frequency or the second frequency, and, in response to the determining, identifying whether the first nucleotide precursor or the second nucleotide precursor has been detected.

In some embodiments, detecting the frequency of the signal generated by the at least one of the plurality of STOs comprises collecting samples of the signal generated by the at least one of the plurality of STOs, and applying a Fourier transform to the samples. In some embodiments, detecting the frequency of the signal generated by the at least one of the plurality of STOs comprises collecting samples of the signal generated by the at least one of the plurality of STOs, and determining frequency content of the samples.

In some embodiments, detecting the frequency of the signal generated by the at least one of the plurality of STOs comprises mixing the signal generated by the at least one of the plurality of STOs with a first reference signal of approximately the first frequency, and mixing the signal generated by the at least one of the plurality of STOs with a second reference signal of approximately the second frequency. In some such embodiments, determining whether the frequency of the signal generated by the at least one of the plurality of the STOs matches the first frequency or the second frequency comprises identifying the frequency of the signal generated by the at least one of the plurality of STOs as the first frequency in response to a result of the mixing being greater than a first threshold, and identifying the frequency of the signal generated by the at least one of the plurality of STOs as the second frequency in response to a result of the mixing being greater than the first threshold or a second threshold.

In some embodiments, determining whether the frequency of the signal generated by the at least one of the plurality of the STOs matches the first frequency or the second frequency comprises determining whether the frequency of the signal generated by the at least one of the plurality of STOs is approximately the first frequency or approximately the second frequency.

In some embodiments, an apparatus for molecule detection comprises at least one fluidic channel, a plurality of STOs, each of the plurality of STOs configured to generate a RF signal in response to detecting a MNP labeling a molecule to be detected within the at least one fluidic channel, means for determining that at least one of the plurality of STOs is generating the RF signal, and means for determining, in response to determining that the at least one of the plurality of STOs is generating the RF signal, that the molecule to be detected has been detected. In some such embodiments, the means for determining that the at least one of the plurality of STOs is generating the RF signal comprises a super-heterodyne circuit coupled to the at least one of the plurality of STOs.

In some embodiments, an apparatus for molecule detection comprises at least one fluidic channel, a plurality of STOs, each of the plurality of STOs configured to cease to generate a RF signal in response to detecting a MNP labeling a molecule to be detected within the at least one fluidic channel, means for determining that at least one of the plurality of STOs is not generating the RF signal, and means for determining, in response to determining that the at least one of the plurality of STOs is not generating the RF signal, that the molecule to be detected has been detected. In some embodiments, the means for determining that the at least one of the plurality of STOs is not generating the RF signal comprises a super-heterodyne circuit coupled to the at least one of the plurality of STOs.

BRIEF DESCRIPTION OF THE DRAWINGS

So that the manner in which the above-recited features of the present disclosure can be understood in detail, a more particular description of the disclosure is in reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 6A, 6B, and 6C illustrate a cross-point array architecture of sensor elements in accordance with some embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1A:
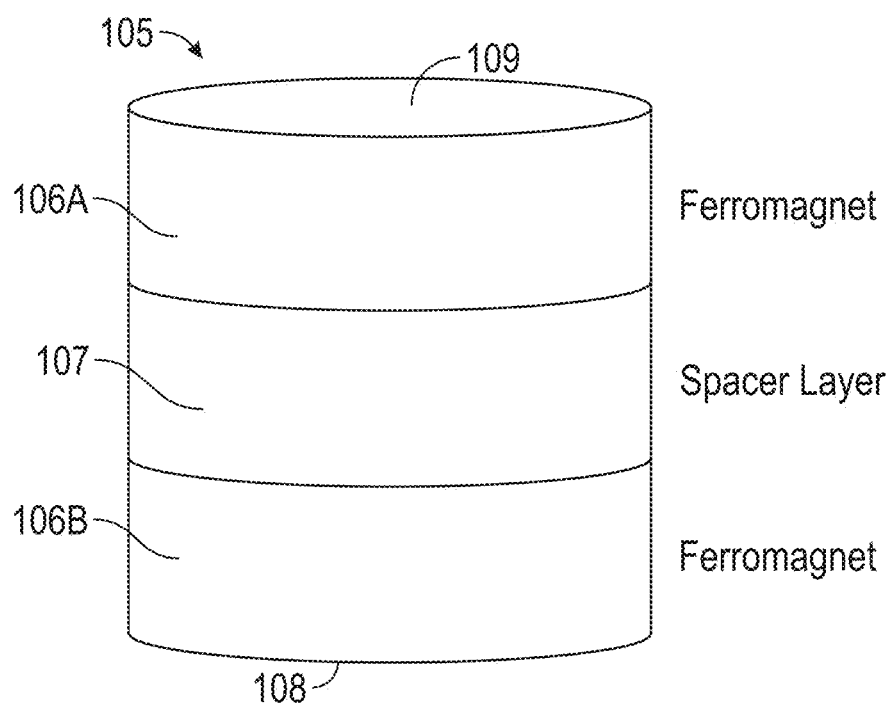
FIG. 1A illustrates a portion of a sensor in accordance with some embodiments.

Disclosed herein are improved detection devices, systems, and methods that use magnetic nanoparticles (MNPs) to allow molecules (e.g., nucleic acids) to be identified. The disclosures herein include embodiments having sensors with spin torque oscillators (STO) that allow for detection of characteristics indicating the presence or absence of MNPs near sensors. Also disclosed herein are detection method embodiments that can be used to detect (e.g., measure or obtain) characteristics or changes in characteristics generated by the sensors indicative of the presence or absence of MNPs (e.g., in response to a magnetic field generated, or not generated, by a magnetic nanoparticle label). For example, devices and methods may determine whether a sensor is or is not generating a signal having a frequency at a particular frequency or within a specified range of frequencies, and, based thereon, determine whether one or more MNPs are being detected by the sensor. As another example, devices and methods may detect a change in a signal generated, or not generated, by a sensor and, based thereon, determine whether one or more MNPs are being detected by the sensor.

As used herein, the term "spin torque oscillator" and acronym "STO" refer to any device that takes advantage of spin-torque-induced precession of magnetization caused by spin polarized currents.

In some embodiments, MNPs are coupled to molecules to be detected. For example, in DNA sequencing applications, the MNPs may label nucleotide precursors that are then incorporated into a target DNA strand affixed to a binding site in the vicinity of a sensor. As a result of the incorporation of a MNP-labeled nucleotide precursor, at least one MNP is in the vicinity of the sensor, and its presence can have an impact on the behavior of the STO. This impact can be detected to detect the presence of the MNP. Presence of the MNP can then be used to determine that a particular nucleotide precursor has been incorporated into the target DNA strand.

In some embodiments, the STO sensors are designed to oscillate at a selected frequency in the presence of a MNP when a bias current is applied to the STOs. Molecules to which MNPs are coupled can then be detected by determining whether the STO is oscillating or not oscillating at the selected frequency. A super-heterodyne detection circuit with a reference oscillator having a frequency approximately the same as the selected frequency may be used to detect whether the STO is oscillating at the selected frequency.

In some such embodiments used for DNA sequencing, a single type of MNP can label different nucleotide precursors. A single-strand DNA to be sequenced can be coupled to a binding site near a sensor having a STO, and a first nucleotide precursor, labeled by the MNP type, can be introduced. If the first nucleotide precursor is incorporated, the STO oscillates at the selected frequency when a bias current is applied, which allows the incorporated nucleotide precursor to be identified. After a chemistry step to cleave and wash away the magnetic label and prepare the DNA strand for the next base pairing, a second nucleotide precursor, labeled by the same MNP type, can be introduced, and the detection procedure repeated. By repeating this process for each of the four nucleotide precursors, each labeled by a the same MNP type, the DNA strand can be sequenced.

In some embodiments, the STOs are designed to oscillate at a selected frequency in the absence of a MNP when a bias current is applied. A procedure similar to the above-described procedure can then be used for DNA sequencing applications, but incorporation of a nucleotide precursor is detected from a lack of oscillation at the selected frequency.

In some embodiments, the STO oscillates at different frequencies in response to different MNP types when a bias current is applied. For example, the magnetic field generated by a first MNP type may cause the STO to oscillate at a first frequency, and the magnetic field generated by a second MNP type may cause the STO to oscillate at a second frequency. By determining the frequency of STO oscillations, one can determine whether the first MNP type is present, whether the second MNP type is present, or whether neither the first nor second MNP type is present.

In some such embodiments used for DNA sequencing, different types of MNPs can label different nucleotide precursors. A single-strand DNA to be sequenced can be coupled to a binding site near a sensor with a STO, and all four nucleotide precursors, each labeled by a different MNP type, can be introduced. If the first nucleotide precursor, labeled by a first MNP type, is incorporated, the STO oscillates at a first frequency when a bias current is applied. If the second nucleotide precursor, labeled by a second MNP type, is incorporated, the STO oscillates at a second frequency when the bias current is applied, and so forth. By detecting the frequency at which the STO oscillates, the identity of the incorporated nucleotide precursor can be determined, and the DNA strand can be sequenced.

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in one or more claims. Likewise, reference to "the disclosure" shall not be construed as a generalization of any inventive subject matter disclosed herein and shall not be considered to be an element or limitation of the appended claims except where explicitly recited in a claim.

It is to be understood at the outset that the disclosures herein may be used to detect any type of molecule to which a magnetic particle can be attached. The disclosure presumes that the particles attached to the molecules to be detected are magnetic nanoparticles, but this presumption is exemplary and is not intended to be limiting. Thus, the term "magnetic nanoparticle" includes all types of magnetic particles that can be attached to molecules to be detected.

Any molecule type that can be labeled by a magnetic nanoparticle may be detected using the devices and methods disclosed herein. Such molecule types may be biologic molecule types, such as proteins, antibodies, etc. For example, the disclosures herein may be used to detect nucleic acids (e.g., in DNA sequencing). The disclosures herein may also be used to detect non-biologic (inorganic or non-living) molecules, such as contaminants, minerals, chemical compounds, etc. The presentation of the disclosure in the context of nucleic acid sequencing is solely exemplary and is not intended to limit the scope of the present disclosure. Accordingly, although some of the disclosure herein is provided in the context of nucleic acid sequencing, and specifically DNA sequencing, it is to be understood that the embodiments herein generally may be used to detect any type of molecule to which a magnetic nanoparticle can be attached.

Furthermore, although the description herein focuses on DNA as an exemplary nucleic acid, the various embodiments described can be applied to nucleic acid sequencing in general. Similarly, although SBS is used for illustrative purposes in the following description, the various embodiments are not so limited to SBS sequencing protocols (e.g., dynamic sequencing could be used instead).

Conventional nucleic acid sequencing, such as that used for DNA sequencing, typically relies on the detection of fluorescence. Specifically, fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, conventional fluorescent sequencing technologies utilize identifiably-distinct fluorescent moieties, each attached to one of the four nucleotides A, T, C, and G that are utilized in a sequencing reaction.

One conventional method of DNA sequencing involves adapting single-strand DNA (ssDNA) for attachment to a solid support of a sequencing apparatus and amplifying the quantity of the ssDNA using techniques such as the polymerase chain reaction to create many DNA molecules with a short leader. An oligo complementary to the short leader may then be added so that there is a short section of double-stranded DNA (dsDNA) at the leader. The double stranded portion of the bound molecule is a primer for a suitable DNA polymerase, such as, for example, Taq polymerase, which is operable at high temperatures.

The sequencing can then take one of several approaches. For example, the sequencing can use a mixture of four fluorescently-labeled 3'-blocked dNTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different fluorescent label), and the different labels are distinguishable by fluorescent spectroscopy or by other optical means.

Four fluorescently-labeled nucleotide precursors can be used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging.

Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors (wavelengths). Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

As explained previously, the disclosures herein may be used to detect any type of molecule (e.g., biologic, organic, inorganic, or non-living) to which a magnetic particle (e.g., a MNP) can be attached. Apparatuses and methods disclosed herein use MNPs and sensors to perform detection of molecules, such as in nucleic acid sequencing (e.g., DNA sequencing using SBS chemistry methods). Specifically, embodiments of this disclosure include sensors comprising STOs that can be used to detect magnetic fields (or changes in magnetic fields) emitted by MNPs, and, specifically to distinguish between the presence and absence of magnetic fields emitted, or not emitted, by MNPs near the sensors. Embodiments that use the same MNP type for all molecules to be detected are disclosed, as are embodiments that use multiple MNP types, each type labeling a different molecule type. The disclosed embodiments allow different types of molecules to be distinguished.

Embodiments of the present disclosure also include various detection methods to obtain or determine (e.g., measure) characteristics of or outputs from the sensors (e.g., presence or absence of oscillations at a particular frequency, and/or a change in oscillation frequency) caused by MNPs used as labels being near the sensors. Knowledge of which particular molecule type (e.g., in DNA sequencing applications, the type of nucleotide precursor) to which the particular MNP label has been attached may then be used to identify the particular molecule type (e.g., in DNA sequencing applications, the last-paired base of the ssDNA strand that is complementary to the identified nucleotide precursor).

STO Sensors

In some embodiments disclosed herein, a spin torque oscillation magnetoresistive sensor is provided to sense magnetic fields caused by MNPs coupled to molecules being detected. The sensor is configured to detect a change in, or a presence or absence of, a precessional oscillation frequency of a magnetization of a magnetic layer to sense the magnetic field of a MNP. The sensor can include a magnetic free layer, a magnetic pinned layer, and a non-magnetic layer between the free and pinned layers. In operation, detection circuitry coupled to these layers induces an electrical (DC) current through the layers. Spin polarization of electrons traveling through the sensor causes a spin-torque-induced precession of the magnetization of one or more of the layers. The frequency of this oscillation changes in response to a magnetic field generated by a MNP in the vicinity of the sensor. In some embodiments, knowledge of how a particular type of MNP changes the frequency of oscillations of the sensor allows the oscillation frequency to be detected to detect the presence, or absence, of the magnetic field and, therefore, the MNP. In some embodiments, the effect of a particular type of MNP on the oscillation frequency of the sensor is known. For example, the particular type of MNP may cause the sensor to oscillate at a frequency f1, and the presence or absence of a signal from the sensor at or near the frequency f1 is used to detect the presence or absence of the particular type of MNP in the vicinity of the sensor.

FIG. 1A illustrates a tri-layer structure of a sensor 105 in accordance with some embodiments. The exemplary sensor 105 of FIG. 1 has a bottom 108 and a top 109. The sensor 105 comprises a STO, which is a patterned magnetic device with an active area including three layers, shown in FIG. 1A as two ferromagnetic (FM) layers 106A, 106B separated by a nonmagnetic spacer layer 107.

In some embodiments, the FM layers 106A, 106B are engineered to have their magnetic moments oriented either substantially in the plane of the film or substantially perpendicular to the plane of the film. Suitable materials for use in the FM layers 106A, 106B include, for example, alloys of Co, Ni, and Fe (sometimes mixed with other elements). The example materials described above are merely exemplary and are not intended to be limiting. Materials suitable for use in the FM layers 106A, 106B are known to those having ordinary skill in the art.

The nonmagnetic spacer layer 107 may be, for example, a metallic material or combination of metallic materials, such as, for example, copper or silver, in which case the structure is called a spin valve (SV). Alternatively, the nonmagnetic spacer layer 107 may be an insulator material such as, for example, alumina (also known in the art as aluminum oxide) or magnesium oxide, in which case the structure is referred to as a magnetic tunnel junction (MTJ). The materials identified for the insulator material are merely exemplary and are not intended to be limiting. Materials suitable for use in the nonmagnetic layer 107 are known to those having ordinary skill in the art.

The active region of the sensor 105 lies in the tri-layer structure shown in FIG. 1A. As described further below in the discussion of FIG. 1B, additional layers may be added above and below the layers 106A, 106B, 107 shown in FIG. 1A to serve various purposes, such as, for example, interface smoothing, texturing, and protection from processing used to pattern the overall detection device (e.g., as shown and described below in the context of, e.g., FIGS. 4A-4C, 5A-5D, etc.) and passivation/protection of the sensor 105. Accordingly, a component that is in contact with a magnetic sensor 105 may be in contact with one of the three illustrated layers 106A, 106B, or 107, or it may be in contact with another part of the sensor 105 that is not illustrated in FIG. 1A.

As described further below, the magnetic moment of one or both FM layers 106A, 106B of the sensor 105 can be excited into precessional orbits by applying an electric current to the device through an effect known as spin transfer. Spin transfer (or spin torque transfer, as it is sometimes called) involves the interaction of a spin polarized current (i.e., a current that has some large fraction of electrons with spins oriented in the same direction) with a FM layer (e.g., 106A, 106B).

Figure 1B:
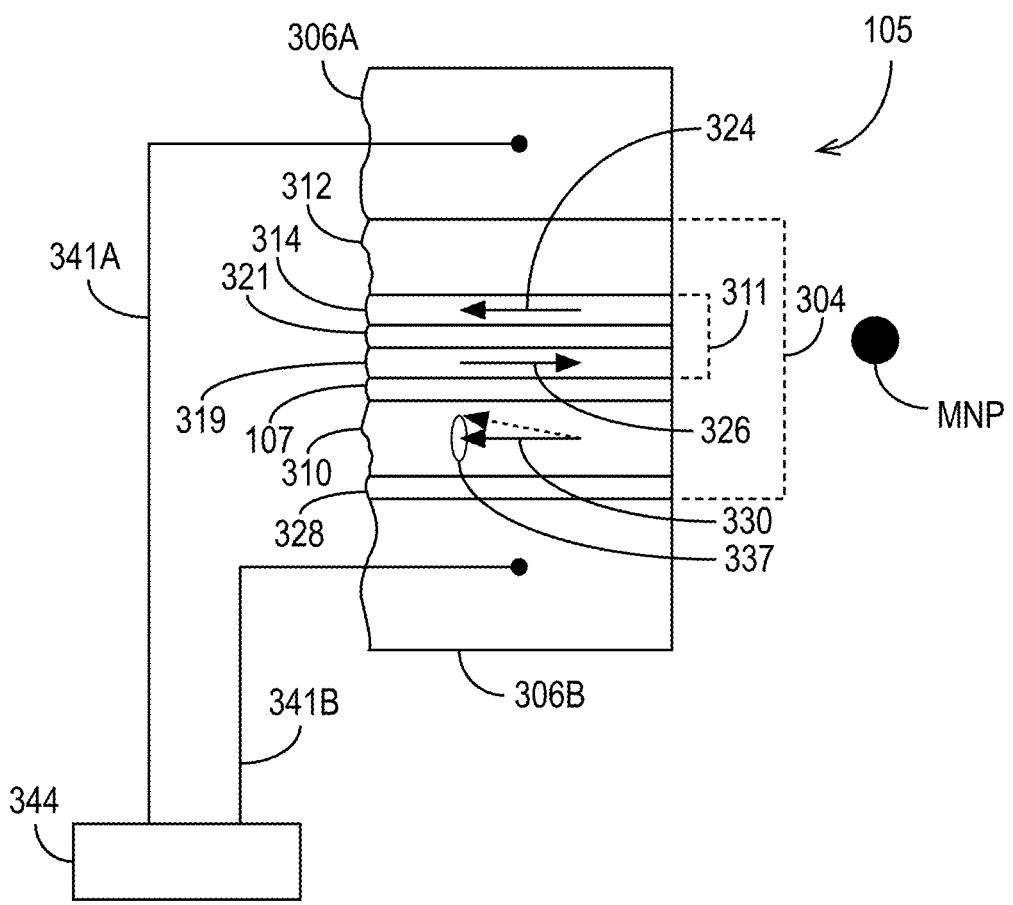
FIG. 1B illustrates an exemplary sensor that can take advantage of spin torque oscillations to sense a localized magnetic field caused by a magnetic particle in accordance with some embodiments.

FIG. 1B is a view of another exemplary sensor 105 that can take advantage of spin torque oscillations to sense a localized magnetic field caused by a magnetic particle (e.g., a MNP). FIG. 1B shows a cross-sectional view of the sensor 105 with the MNP being sensed shown located to the right of the sensor 105.

The exemplary sensor 105 of FIG. 1B includes a sensor stack 304 that is sandwiched between optional first and second magnetic shields 306A, 306B. If present, the magnetic shields 306A, 306B can be made of an electrically conductive, magnetic material such as NiFe so that they can function as electrical leads as well as magnetic shields. The sensor stack 304 includes a pinned layer structure 311, a free layer 310, and a non-magnetic spacer layer 107 sandwiched between the free layer 310 and the pinned layer structure 311. As explained above in the context of FIG. 1A, the non-magnetic spacer layer 107 can be a non-magnetic, electrically conducting spacer layer, or it can be a thin, non-magnetic, electrically-insulating barrier layer. A capping layer 328 (e.g., comprising tantalum) can be situated adjacent to the free layer 310 as shown in FIG. 1B. It is to be appreciated that FIG. 1B shows the sensor 105 with an exemplary orientation of layers (e.g., the pinned layer structure 311 above the free layer 310), but that other orientations are possible (e.g., the pinned layer structure 311 can be below the free layer 310, the sensor 105 can be rotated relative to how it is shown in FIG. 1B, some of the elements shown in FIG. 1B (e.g., shields 306A, 306B) can be omitted, etc.).

The pinned layer structure 311 can include a magnetic pinned layer 314, a reference layer 319, and a non-magnetic antiparallel coupling layer 321 sandwiched between the pinned layer 314 and the reference layer 319. The pinned and reference layers 314, 319 can comprise a material such as, for example, CoFe, and the antiparallel coupling layer 321 can comprise a material such as, for example, Ru having a thickness of, for example, about 10 Angstroms. The pinned layer 314 can be exchange coupled with a layer of antiferromagnetic material, AFM layer 312, which can comprise a material such as, for example, IrMn, PtMn, or some other suitable antiferromagnetic material. Exchange coupling between the AFM layer 312 and the pinned layer 314 strongly pins the magnetization 324 of the pinned layer 314 in a first direction as indicated. Strong antiparallel coupling between the pinned and reference layers 314, 319 pins the magnetization 326 of the reference layer 319 in a second (antiparallel) direction as indicated.

In the exemplary embodiment shown in FIG. 1B, the free layer 310 has its magnetization 330 biased in a direction that is substantially anti-parallel to the magnetization 326 of the reference layer 319. In some embodiments, in the quiescent state of the magnetization (e.g., when the STO is not oscillating), the magnetization 330 of the free layer 310 is at a modest angle relative to the magnetization 326 of the reference layer 319. This can be seen with reference to FIG. 1C, which shows an exploded schematic view of the reference layer 319 and free layer 310. As shown, the reference layer 319 has a magnetization 326 that is pinned in a direction that is parallel (or antiparallel) to an applied magnetic field 327, but the free layer 310 has a magnetization 330 that is biased in a direction that is nearly antiparallel to the direction of the reference layer magnetization 326, but may be is offset by an angle 329. The angle 329, if present, is generally about 20-60 degrees but may be as large as nearly 90 degrees. Biasing of the free layer 310 can be provided by hard magnetic bias layers that are not shown in FIG. 1B, but would be into and out of the page in FIG. 1B. While the free layer 310 is magnetically biased, the magnetization 330 of the free layer 310 is free to move in a precessional spin torque oscillation 337 as indicated in FIG. 1B and as discussed previously.

With reference again to FIG. 1C, canting of the free layer 310 magnetization 330 direction with respect to the magnetization 326 direction of the reference layer 319 can be provided by a magnetic anisotropy having a component oriented perpendicular to the direction of magnetization 326 of the reference layer 319, and/or perpendicular to a direction of an applied magnetic field 327. This magnetic anisotropy can be produced by a layer of antiferromagnetic material that is weakly exchange coupled with the free layer 310, or by shape anisotropy, or by a texture induced magnetic anisotropy. The canting of the free layer 310 can also be achieved by placement of high coercivity magnetic material near the free layer 310 and with magnetization having a substantial component perpendicular to the reference layer 319, in analogy to the hard bias structures that may be used in recording heads to stabilize the free layer of GMR and TMR readback sensors. These are by way of example, however; other mechanisms could be used as well.

As described in further detail below, when a high current density of spin-polarized electrons generated by one magnetized layer impinges upon a second magnetized layer, spin torque effects are observed, and these spin torque effects dynamically excite the second layer's magnetization through a mechanism called spin transfer. Here, electrons traveling through the ferromagnet tend to have their spins aligned parallel to the magnetization of the ferromagnet, losing any component of spin angular momentum transverse to the magnetization. To conserve angular momentum, the polarized current must then exert a torque upon the magnetization.

Figure 2A:
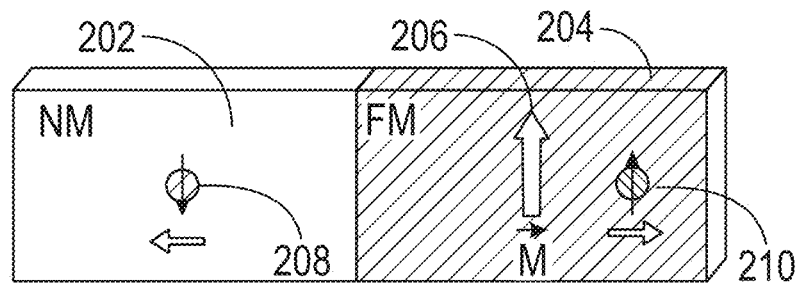
FIGS. 2A, 2B, and 2C illustrate how electrons in an electric current interact with thin-film ferromagnetic layers in accordance with some embodiments.
Figure 2B:
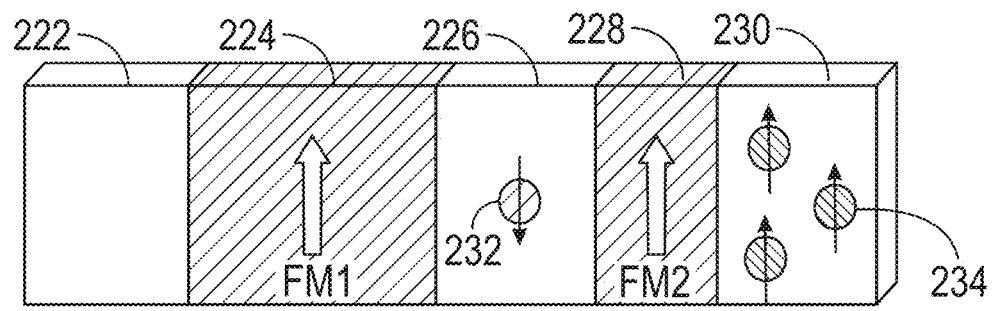
Figure 2C:
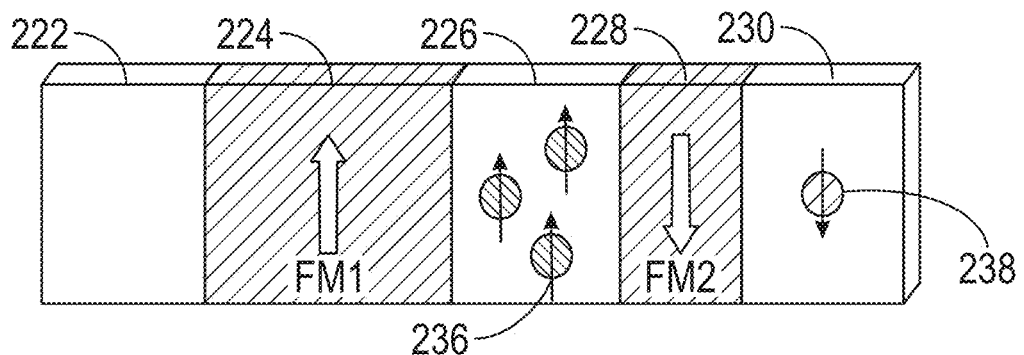

FIGS. 2A through 2C illustrate in further detail how an electron in an electric current interacts with thin-film FM layers. Quantum mechanics dictate that the probability is high that an electron interacting with a FM layer will cause the electron spin to be oriented preferentially parallel or antiparallel to the direction of the FM layer's moment for transmitted and reflected electrons respectively. As shown in FIG. 2A, electrons with spin 210, which is parallel to the moment 206 of the FM layer 204, preferentially pass through the FM layer 204, whereas those with spin 208, which is antiparallel to the moment 206 of the FM layer 204, preferentially are reflected back. Due to this phenomenon, the interface between a nonmagnetic (NM) layer 202 (assumed for purposes of this explanation to be a metal layer, although, as discussed above, the NM layer 202 may alternatively be an insulator) and a FM layer 204 acts as a spin filter that can act to spin polarize (i.e., make one spin direction more preferential) an incoming electric current.

For a device with two FM layers 224 and 228 separated by a nonmagnetic metal layer 226 (spacer layer), as shown in FIGS. 2B and 2C, an incoming electric current spin polarized by the first FM layer (FM1) 224 interacts differently with the second FM layer (FM2) 228, depending on the orientation of the second FM layer 228's magnetic moment. If the moments of both FM layers 224 and 228 are parallel to one another (FIG. 2B), then many electrons will pass through the device because many electrons in the current will have their spin oriented with the moment of the second FM layer 228 (spin 234). Few electrons will be reflected back (spin 232).

In the opposite case, when the moments of the two FM layers 224 and 228 are oriented in an anti-parallel fashion (FIG. 2C), many electrons will be blocked from passing through the second FM layer 228 (spin 236), and far fewer electrons will traverse the device (spin 238). This means the amount of current passing through the device is dependent on the orientation of the moments of the two FM layers 224 and 228 with respect to one another. Because the resistance of the device that includes FM layers 224 and 228 and NM layer 226 is inversely proportional to the current, the resistance of the device is dependent on the orientation of the moments of the two FM layers 224 and 228 (i.e., the resistance is smaller when the moments are parallel than it is when they are antiparallel).

Whereas the above description presumes use of a non-magnetic metal layer 226 separating the two FM layers 224 and 228 (a configuration also known as a spin valve (SV) or giant magnetoresistance (GMR) device), an insulating layer known as a tunneling barrier can alternatively be used as the spacer layer (e.g., instead of NM layer 226) separating the FM layers 224, 228. In such implementations, the spacer layer may be made of oxide-based material. These types of devices are called magnetic tunnel junctions (MTJs), and they exhibit a similar resistance response (referred to as tunnel magnetoresistance or TMR) because of spin polarized tunneling as opposed to spin filtering.

Referring again to FIG. 1B, with electrons flowing from the reference layer 319 through the non-magnetic spacer layer 107 to the free layer 310, the spin of the electrons flowing through the reference layer 319 are polarized by the magnetization 326 of the reference layer 319. These polarized electrons can then apply a torque to the free layer magnetization 330, generating spin waves that result in chaotic magnetization dynamics (noise) or collective excitations (oscillations), depending on various parameters of the system such as sensor 105 shape, anisotropy, layer materials and thicknesses, and applied currents and magnetic fields.

As explained above, spin torque oscillations involve spin-torque-excited precession of the magnetization along the equilibrium axis of the ferromagnet. For example, with reference to FIG. 1B, the precession, or oscillation, of the magnetization 330 is indicated by oscillation 337. Note that although the pinned layer 314 magnetization 324 is constrained by exchange anisotropy to an antiferromagnetic layer 312, it is possible for the magnetization of the pinned layer 314 to oscillate as well, and to contribute to the sensor 105 signal when the applied current densities are high enough to generate spin torque excitations in the pinned layer 314.

The frequency of this precession (oscillation frequency) shifts with the application of a magnetic field. With a suitable selection of sensor materials and geometry, this shift can be very large. Frequency shifts up to 180 GHz/T have been demonstrated, and higher values are possible. Some embodiments described herein take advantage of these frequency shifts to detect the change in magnetic field at the free layer 310 induced by magnetic nanoparticles in the vicinity of the sensor 105.

Referring to FIG. 1B, the sensor 105 is connected via leads 341A, 341B to processing circuitry 344. The leads 341A, 341B, which may be magnetic or nonmagnetic, can be connected with the optional shield/lead layers 306A, 306B (if present) such that one lead 341A is connected with one lead/shield layer 306A, while the other lead 341B is connected with the other lead/shield layer 306B. The processing circuitry 344 sends a sense (bias) current through the sensor stack 304 and also measures the electrical resistance across the sensor stack 304. As those skilled in the art will appreciate, the electrical resistance across the nonmagnetic spacer layer 107 changes as the orientation of the magnetization 330 of the free layer 310 changes relative to the magnetization 326 of the reference layer 319. The closer these magnetizations 330, 326 are to being parallel, the lower the electrical resistance will be. Conversely, the closer these magnetizations 330, 326 are to being anti-parallel, the higher the electrical resistance will be. The resistance of the device effectively acts as a magnetic-field-to-voltage transducer.

The presence of a MNP in the vicinity of the sensor 105 causes the above-described change in the frequency of the oscillation 337 of the magnetization 330. As the magnetization 330 oscillates, the frequency of this oscillation 337 can be measured by the processing circuitry 344 by measuring the change of electrical resistance across the sensor stack 304. In addition or alternatively, the presence or absence of oscillation 337 at a particular frequency can be detected to determine whether a MNP is in the vicinity of the sensor 105. Therefore, in accordance with some embodiments disclosed herein, the spin torque oscillation is used to detect the presence or absence of a magnetic field caused by magnetic nanoparticles.

Figure 3A:
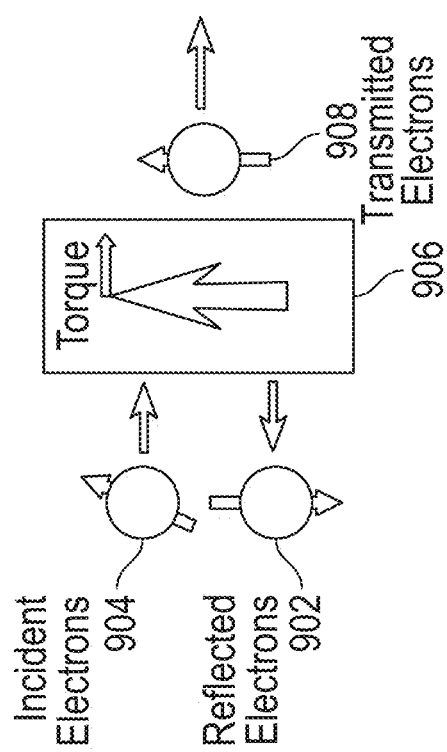
FIGS. 3A, 3B, and 3C illustrate operating principles of STO-based sensors in accordance with some embodiments.
Figure 3B:
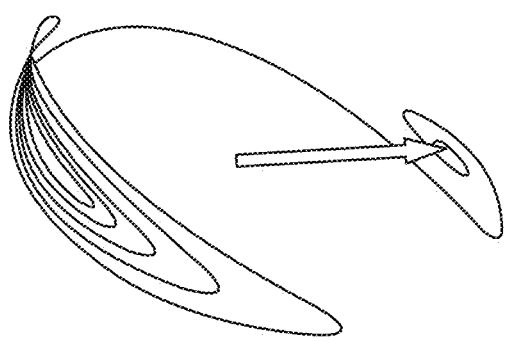
Figure 3C:
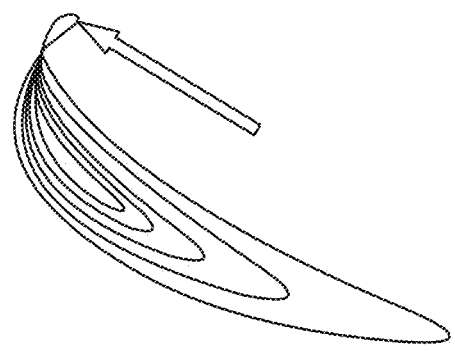

FIGS. 3A through 3C further illustrate the basic operating principles of STO-based sensors 105. FIG. 3A shows how incident electrons 904 with arbitrary spin direction either transmit through or are reflected by a FM layer 906. As shown, those incident electrons 904 with spin parallel to the magnetic moment of the FM layer 906 are transmitted electrons 908, whereas incident electrons 904 with spin anti-parallel to the magnetic moment of the FM layer 906 are reflected electrons 902. Any spin angular momentum lost becomes a torque acting on the FM layer 906. The torque from a single electron interaction is small, but for a spin polarized current on the order of a milli-Ampere, there are approximately $10^{15}$ electrons interacting with the FM layer 906 per second. Thus, the net torque on the FM layer 906 can be sufficient to induce the moment into a dynamic mode. These dynamics are governed by the Landau-Lifshitz-Gilbert-Slonczewski (LLGS) equation:

$$\frac{d\hat{m}}{dt} = -\gamma \hat{m} \times \vec{H}_{eff} + \alpha \hat{m} \times \frac{d\hat{m}}{dt} + \frac{\eta I}{|m|} \hat{m} \times \hat{p} \times \hat{m}$$

where $\gamma$ is the gyromagnetic ratio, $\hat{m}$ is the normalized moment vector, $\vec{H}_{eff}$ is the effective magnetic field acting on the FM layer 906, $\alpha$ is the phenomenological Gilbert damping parameter, $\eta$ is spin polarization of the current I, and $\hat{p}$ is the direction of the current's spin polarization.

The first term in the equation, called the Larmor precession term, indicates that in the absence of any damping, the moment of the FM layer 906 will precess around the effective magnetic field acting on the FM layer 906. However, the second term (Gilbert damping) comes from intrinsic damping occurring in every ferromagnet that acts to damp out any dynamics of the moment. The final term is the Slonczewski spin torque term that acts like either a damping or anti-damping term, depending on the polarity of the applied electric current. In the case of anti-damping, the spin torque will entirely cancel out the Gilbert damping at a sufficient current amplitude and will result in magnetization oscillations as shown in FIG. 3C. As the current amplitude further increases, the oscillation amplitude also increases, eventually causing the moment to cross points 90 degrees from equilibrium. In this region, the cross product in the Slonczewski term changes sign and acts to damp out the motion such that the moment will rotate 180 degrees from the original position, as shown in FIG. 3B.

Thus, considering a full STO device similar to that described above, with one FM layer 906 excited through spin transfer effects and a second FM layer 906 with a moment fixed in some chosen direction (they are co-linear), a STO excited as shown in FIG. 3C will produce a radio-frequency (RF) voltage signal from an applied DC current due to resistance fluctuations (and, therefore, voltage and current fluctuations) caused by magnetoresistive effects. The frequency of the generated RF signal can be on the order of GHz.

Figure 1C:
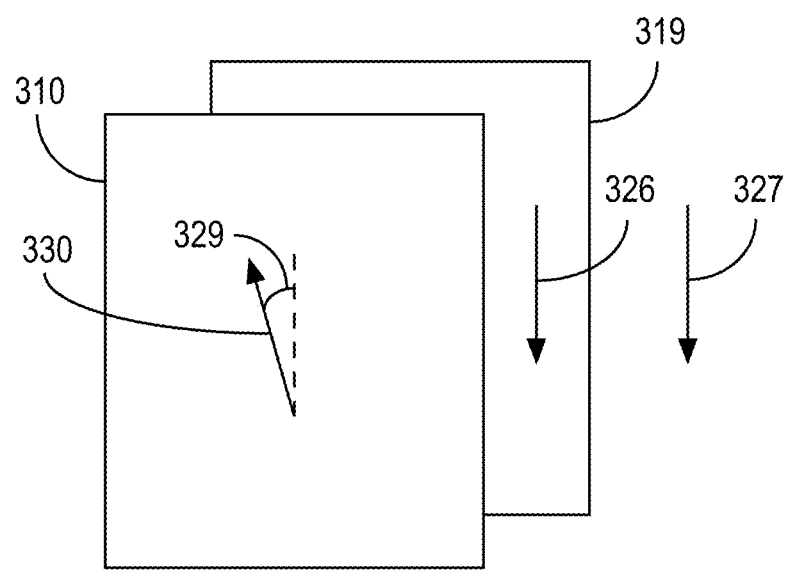
FIG. 1C shows an exploded schematic view of a sensor's reference layer and free layer in accordance with some embodiments.

Taking advantage of these operational principles for detection, some embodiments disclosed herein involve an array of sensors 105 comprising STO devices, such as the sensors 105 shown in FIGS. 1A, 1B, and 1C and the arrays shown in, for example, FIGS. 4A-4C, 5A-5D, etc. Each of the sensors 105 of the sensor array may be used to detect magnetic particles (e.g., MNPs) in a fluidic channel of a detection device. Each sensor 105 may have dimensions of less than about 30 nm to detect magnetic fields on the order of a few millitesla (mT). In some embodiments, individual sensors 105 in a sensor array are configured to generate a RF signal only within a narrow band of magnetic fields (e.g., around zero applied field, although that is not required), for example between 50 and −50 Oe. In some embodiments, individual sensors 105 in a sensor array are configured to generate a RF signal in the presence of larger applied fields.

In DNA sequencing applications, nucleotide precursors (or, more generally, nucleic acids) labeled by MNPs and incorporated by polymerase may be detected by determining whether the sensor 105 is generating a RF signal within a specified frequency band. For example, in some embodiments, the sensor 105 generates a RF signal at or near a particular frequency in the absence of a MNP, but in the presence of a MNP labeling the DNA base (or a nucleotide precursor incorporated in a target DNA strand being sequenced), the local magnetic field is sufficient to "turn off" the STO at and around that frequency (e.g., the local magnetic field may shift the frequency of the RF signal). In other embodiments, the sensor 105 generates a RF signal in the presence of the MNP, but is otherwise "off" in the absence of MNPs. Accordingly, it is to be appreciated that detection may be performed using sensors 105 comprising STOs designed to "turn on" and generate a RF signal at a particular frequency or within a particular frequency band only in the presence of an applied magnetic field generated by one or more MNPs in the vicinity of the sensor 105, or to "turn off" and generate a RF signal at a particular frequency or within a particular frequency band only in the absence of an applied magnetic field generated by one or more MNPs in the vicinity of the sensor 105.

An advantage of performing detection using sensors 105 comprising STO devices is that the MNPs used as labels may be either superparamagnetic (e.g., thermally unstable such that the magnetic field generated fluctuates over time) or ferromagnetic. Moreover, the use of STOs does not require the moments of individual MNPs to be aligned in the same direction (e.g., detection may be accomplished without use of an external magnetic field). One benefit of superparamagnetic particles is that they are not ferromagnetic and will not stick to or attract each other appreciably when introduced into a flow cell of a detection device (e.g., the fluidic channels described below in the context of, e.g., FIGS. 4A-4C and 5A-5D).

Detection Devices

Figure 4A:
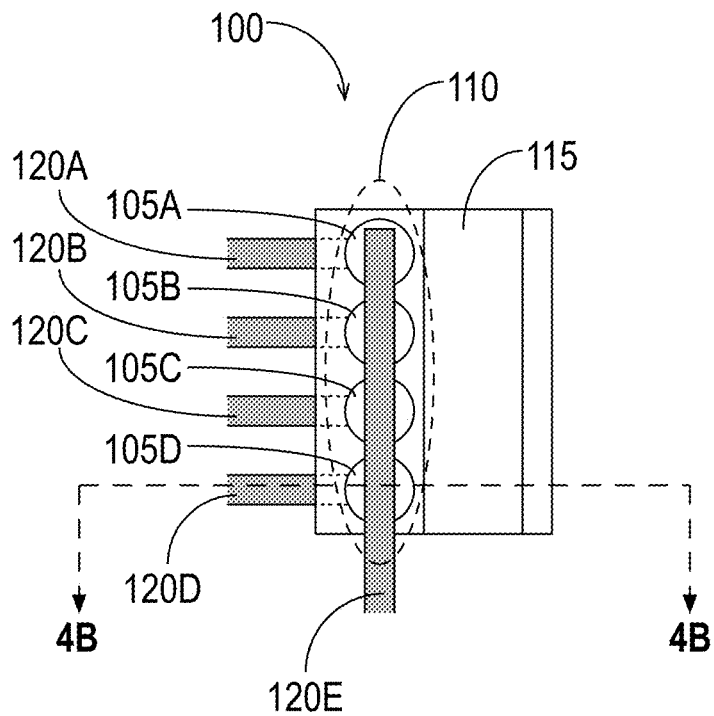
FIGS. 4A, 4B, and 4C illustrate an apparatus for molecule detection in accordance with some embodiments.
Figure 4B:
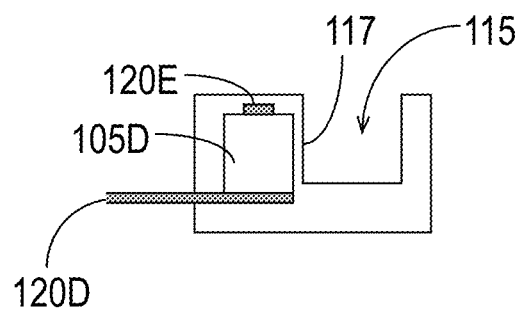
Figure 4C:
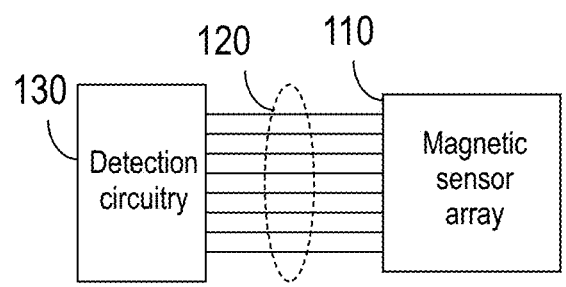

The STO-based sensors 105 described above may be incorporated into an apparatus for the detection of molecules that are coupled to respective magnetic nanoparticles (e.g., for nucleic acid sequencing). FIGS. 4A, 4B, and 4C illustrate a detection device 100 that may be used, e.g., for nucleic acid sequencing in accordance with some embodiments. FIG. 4A is a top view of the apparatus, and FIG. 4B is a cross-section view at the position indicated in FIG. 4A. FIG. 4C is a block diagram showing components of the detection device 100. As shown in FIG. 4A, the exemplary detection device 100 comprises a sensor array 110 that includes a plurality of sensors 105, with four sensors 105A, 105B, 105C, and 105D shown in FIG. 4A. (For simplicity, this document refers generally to the sensors by the reference number 105. Individual sensors are given the reference number 105 followed by a letter.) The sensor array 110 shown in the exemplary embodiment of FIG. 4A is a linear array.

In some embodiments, each of the plurality of sensors 105 is coupled to at least one line 120 for reading a characteristic of or output from one or more of the sensors 105 (e.g., detecting whether a sensor 105 is oscillating, determining whether a sensor 105 is oscillating at a particular frequency, etc.). (For simplicity, this document refers generally to the lines by the reference number 120. Individual lines are given the reference number 120 followed by a letter.) In the exemplary embodiment shown in FIG. 4A, each sensor 105 of the sensor array 110 is coupled to two lines 120. Specifically, the sensor 105A is coupled to the lines 120A and 120E, the sensor 105B is coupled to the lines 120B and 120E, the sensor 105C is coupled to the lines 120C and 120E, and the sensor 105D is coupled to the lines 120D and 120E. The lines 120A, 120B, 120C, and 120D reside under the sensors 105A, 105B, 105C, and 105D, respectively, and the line 120E resides over the sensors 105. FIG. 4B shows the sensor 105D in relation to the lines 120D and 120E.

The detection device 100 also includes a fluidic channel 115 (which may also be referred to as a nanochannel or flow cell) that is adjacent to the sensor array 110. As its name suggests, the fluidic channel 115 is configured to hold fluids (e.g., liquids, gases, plasmas) when the detection device 100 is in use. The fluidic channel 115 may by open (e.g., if its shape is rectangular, it may have three sides; if its shape is curved, it may have a shape that is a portion of a cylinder; etc.) or closed (e.g., if its shape is rectangular, it may have four sides; if its shape is curved, it may be cylindrical; etc.). The shape of the fluidic channel 115 may be regular or irregular along its length. The fluidic channel 115 may be coupled to a device (e.g., a pump) that forces fluids into the fluidic channel 115. Alternatively, the fluidic channel 115 may not be coupled to a device that injects or removes fluids.

As shown in FIG. 4B, the fluidic channel 115 has a wall 117 that is adjacent to the sensor array 110. The wall 117 may be referred to as a proximal wall. The wall 117 may be substantially vertical as illustrated in FIG. 4B. Alternatively, the wall 117 may be sloped at least in part (e.g., some or all of the interior of the fluidic channel 115 may be at an angle that is not 90 degrees, or it may be curved (e.g., in the shape of a portion or all of a cylinder)). In general, the fluidic channel 115 and wall 117 may have any shapes that allow the sensors 105 to detect the presence of magnetic particles on the other side of the wall 117 that are within the fluidic channel 115.

When the detection device 100 is in use, the sensors 105 are able to detect, through the wall 117, the presence or absence of magnetic nanoparticles (MNPs) that are in the fluidic channel 115. Thus, the wall 117 has properties and characteristics that protect the sensors 105 from whatever fluid is in the fluidic channel 115 while still allowing the sensors 105 to detect MNPs that are within the fluidic channel 115. For example, the material of the wall 117 (and potentially of the rest of the fluidic channel 115) may be or comprise an insulator material. For example, in some embodiments, a surface of the wall 117 comprises polypropylene, gold, glass, and/or silicon. In addition, the thickness of the wall 117 may be selected so that the sensors 105 can detect MNPs within the fluidic channel 115. In some embodiments, the thickness of the wall 117 is between approximately 2 nm and approximately 20 nm.

In some embodiments, the wall 117 has a structure (or multiple structures) configured to anchor or bind molecules to be sensed (e.g., nucleic acid or molecules of a nucleic acid polymerase) to the wall 117. For example, the structure (or structures) of the wall 117 may include a cavity or a ridge or multiple cavities/ridges that provide binding sites associated with the sensors 105.

To simplify the explanation, FIGS. 4A and 4B illustrate an exemplary detection device 100 with a single fluidic channel 115 and only four sensors 105A, 105B, 105C, 105D in the sensor array 110. It is to be appreciated that the detection device 100 may have many more sensors 105 in the sensor array 110, and it may have either additional fluidic channels 115 or a more intricate single fluidic channel 115 (e.g., with a different shape or with interconnected channels). In general, any configuration of sensors 105 and fluidic channel(s) 115 that allows the sensors 105 to detect MNPs in the fluidic channel(s) 115 may be used.

As illustrated in FIG. 4C, the detection device 100 includes detection circuitry 130 coupled to the sensor array 110 via the lines 120. In some embodiments, in operation, the detection circuitry 130 applies a current to the lines 120 to detect a characteristic of or output from at least one of the plurality of sensors 105 in the sensor array 110, where the characteristic or output indicates a presence or an absence of a magnetically-labeled molecule in the fluidic channel 115. For example, in some embodiments, the characteristic or output is a signal or an absence of a signal. The detection circuitry 130 may comprise any suitable components, including, generally, suitable detection circuitry. Such detection circuitry 130 may comprise hardware and/or software. The detection circuitry 130 may include, for example, one or more of: a processor capable of executing machine-executable instructions, an application-specific integrated circuit (ASIC), a controller, a programmable circuit (e.g., FPGA), etc.

As an example of a detection device 100 with a larger number of sensors 105 in the sensor array 110, FIGS. 5A, 5B, 5C, and 5D illustrate portions of an exemplary detection device 100 that includes several channels, one or more of which may be a separate fluidic channel 115 in accordance with some embodiments, or the aggregation of which may be considered a single fluidic channel 115. In the embodiment of the detection device 100 shown in FIGS. 5A, 5B, 5C, and 5D, the plurality of sensors 105 of the sensor array 110 is arranged in a rectangular grid pattern. Each of the lines 120 identifies a row or a column of the sensor array 110. It is to be understood that FIGS. 5A, 5B, 5C, and 5D show only a portion of the detection device 100 to avoid obscuring the parts of the detection device 100 being discussed. It is to be understood that the various illustrated components (e.g., lines 120, sensors 105, fluidic channels 115, etc.) might not be visible in a physical instantiation of the detection device 100 (e.g., some or all may be covered by protective material, such as an insulator material).

Figure 5A:
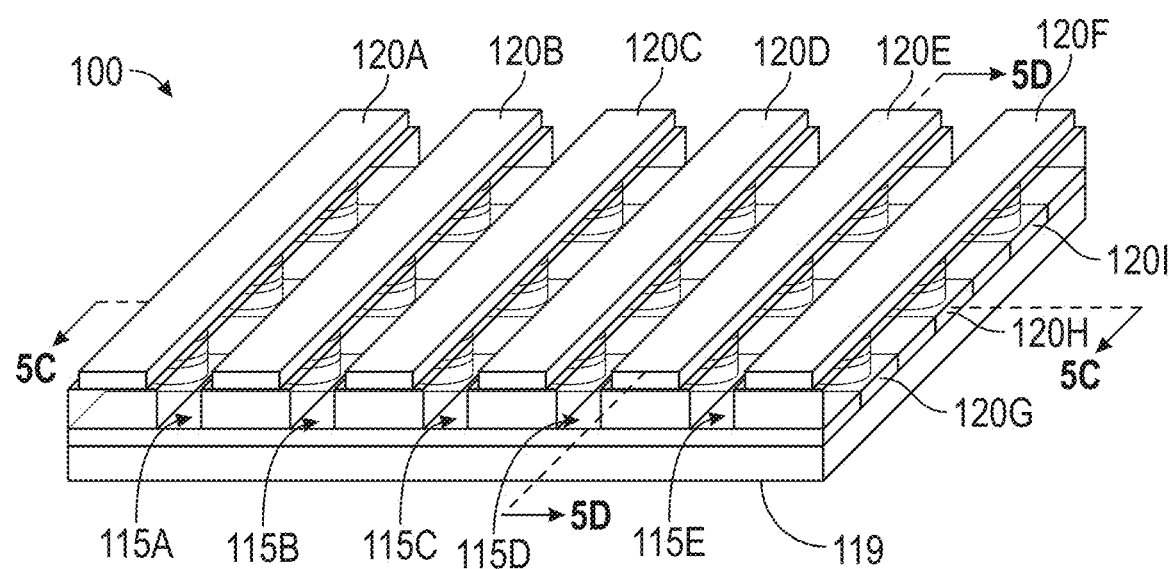
FIGS. 5A, 5B, 5C, and 5D illustrate portions of another exemplary apparatus for molecule detection in accordance with some embodiments.

FIG. 5A is a perspective view of the exemplary detection device 100 in accordance with some embodiments. The detection device 100 includes nine lines 120, labeled as 120A, 120B, 120C, 120D, 120E, 120F, 120G, 120H, and 1201. It also includes five fluidic channels, labeled as 115A, 115B, 115C, 115D, and 115E. As explained above, the fluidic channels 115A, 115B, 115C, 115D, and 115E may be considered to be separate fluidic channels 115 or a single fluidic channel 115. The detection device 100 also has a bottom surface 119.

Figure 5B:
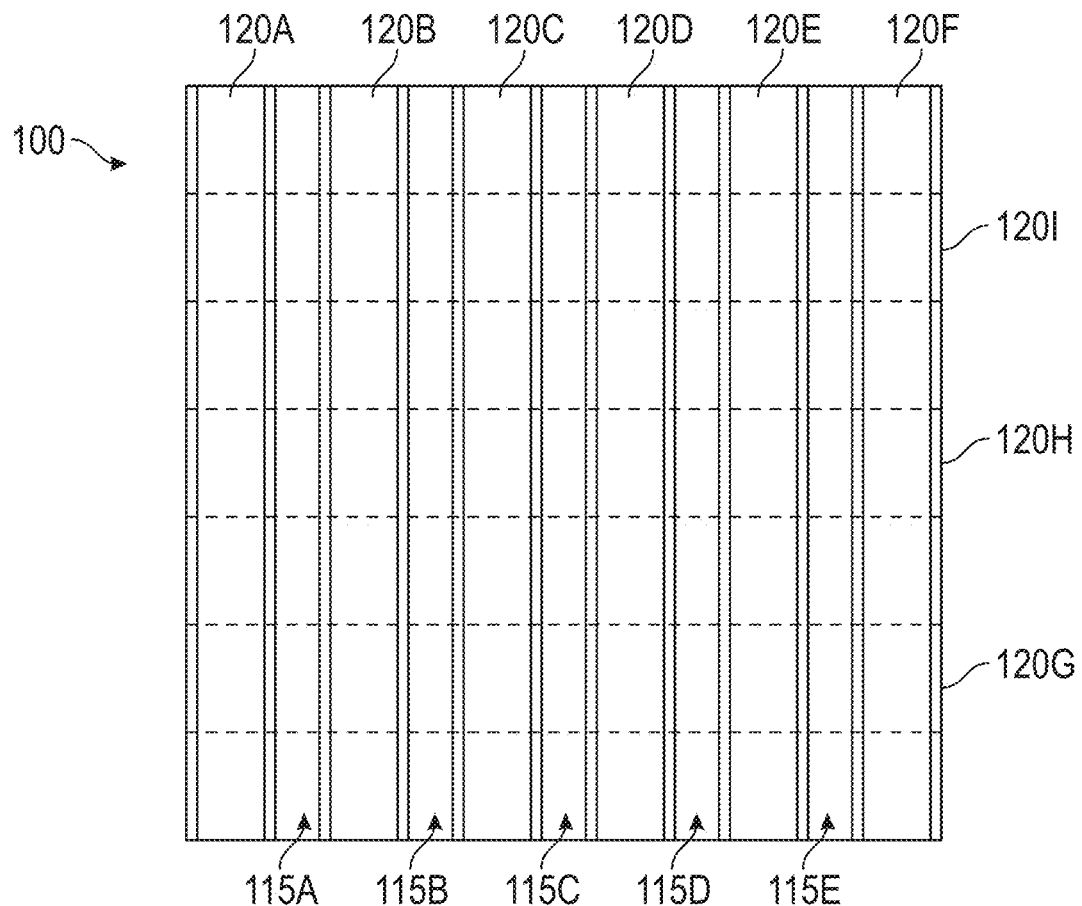

FIG. 5B is a top view of the exemplary detection device 100 from FIG. 5A. The lines 120G, 120H, and 1201, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator material).

Figure 5C:
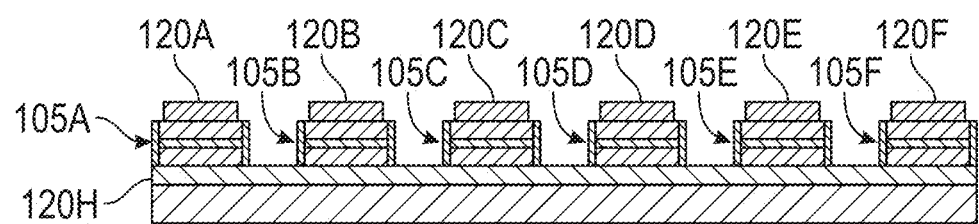

FIG. 5C is a cross-sectional view of the detection device 100 along the line labeled "5C" in FIG. 5A. As shown, each of the lines 120A, 120B, 120C, 120D, 120E, and 120F is in contact with the top of one of the sensors 105 along the cross-section (namely, line 120A is in contact with sensor 105A, line 120B is in contact with sensor 105B, line 120C is in contact with sensor 105C, line 120D is in contact with sensor 105D, line 120E is in contact with sensor 105E, and line 120F is in contact with sensor 105F). The line 120H is in contact with the bottom of each of the sensors 105A, 105B, 105C, 105D, 105E, and 105F. It is to be appreciated that although FIGS. 5A-5D illustrate the lines 120 in contact with the sensors 105, the lines 120 may, in general, be coupled to the sensors 105 (i.e., they may be directly connected, or there may be intervening components disposed between the lines 120 and the sensors 105).

The sensors 105A and 105B are separated by the fluidic channel 115A (unlabeled in FIG. 5C but shown in FIG. 5A). Similarly, the sensors 105B and 105C are separated by the fluidic channel 115B, the sensors 105C and 105D are separated by the fluidic channel 115C, the sensors 105D and 105E are separated by the fluidic channel 115D, and the sensors 105E and 105F are separated by the fluidic channel 115E. As discussed further below, either or both of the vertical walls of each fluidic channel 115 may be the wall 117.

In some embodiments, each sensor 105 is assigned to a single fluidic channel 115. For example, in the exemplary device illustrated in FIGS. 5A-5D, the sensors 105 coupled to the line 120A may be configured to sense MNPs in the fluidic channel 115A, the sensors 105 coupled to the line 120B may be configured to sense MNPs in the fluidic channel 115B, the sensors 105 coupled to the line 120C may be configured to sense MNPs in the fluidic channel 115C, the sensors 105 coupled to the line 120D may be configured to sense MNPs in the fluidic channel 115D, and the sensors 105 coupled to the line 120E may be configured to sense MNPs in the fluidic channel 115E.

In the exemplary embodiment illustrated in FIGS. 5A-5C, there are more columns of sensors 105 than there are fluidic channels 115 (i.e., in the exemplary embodiment shown, there are six columns corresponding to lines 120A-120F and only five fluidic channels 115A-115E). In such embodiments, each vertical wall of one fluidic channel 115 may be the wall 117. In other words, a single fluidic channel 115 may be sensed by twice as many sensors 105 as each of the other fluidic channels 115. For example, in the exemplary embodiment of FIGS. 5A-5D, any of the fluidic channels 115 may be sensed by two columns of sensors 105. For example, the fluidic channel 115B may be sensed by the sensors 105 coupled to both lines 120B and 120C. In this example, the sensors 105 coupled to the line 120A would be assigned to sense the contents of the fluidic channel 115A, the sensors 105 coupled to the line 120D would be assigned to sense the contents of the fluidic channel 115C, the sensors 105 coupled to the line 120E would be assigned to sense the contents of the fluidic channel 115D, and the sensors 105 coupled to the line 120F would be assigned to sense the contents of the fluidic channel 115E.

Figure 5D:
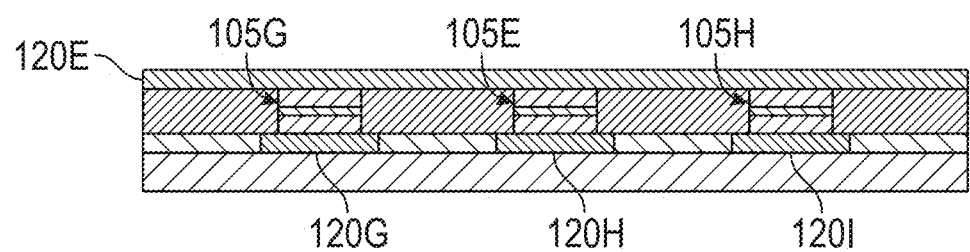

FIG. 5D is a cross-sectional view of the detection device 100 along the line labeled "5D" in FIG. 5A. As shown, the line 120E is in contact with the top of each of the sensors 105G, 105E, and 105H along the cross-section. Each of the lines 120G, 120H, and 120I is in contact with the bottom of one of the sensors 105 along the cross-section (namely, line 120G is in contact with sensor 105G, line 120H is in contact with sensor 105E, and line 120I is in contact with sensor 105H). As explained above, the lines 120 shown in FIG. 5D need not be in direct contact with the sensors 105; instead, they may be connected through intervening components.

In some embodiments (see, e.g., FIGS. 5E, 5F), the detection device 100 includes a plurality of selector elements 111, each of which is coupled to a respective one of the sensors 105, where each of the selector elements 111 exhibits thresholding behavior such that for voltages above a given value (i.e., $V_{th}$) the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the sensors 105 (individually or in groups) can be used that ensure only the voltage dropped across the intended sensor(s) 105 is above $V_{th}$. Accordingly, selector elements 111 may be used reduce the chances of "sneak" currents that could transmit through neighboring elements and degrade the performance of the detection device 100.

Figure 5E:
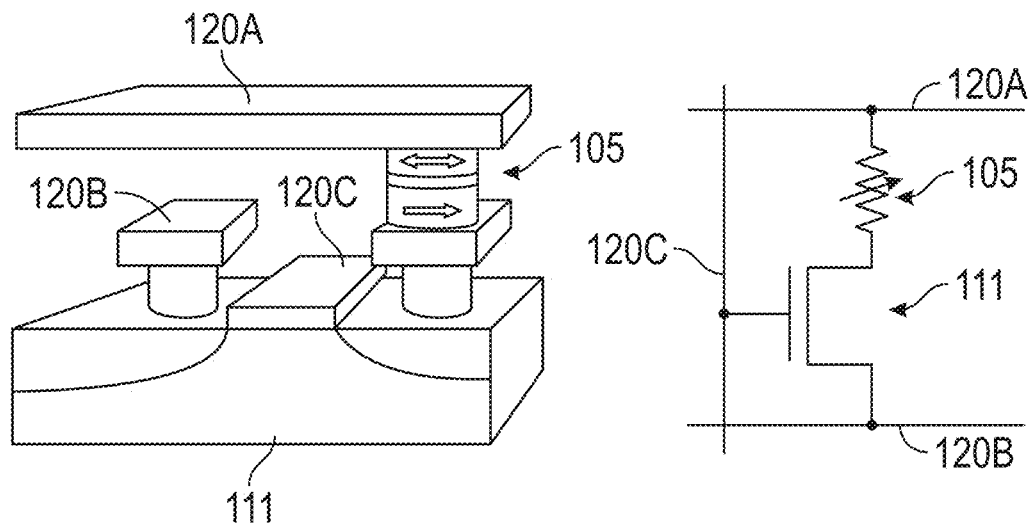
FIG. 5E illustrates a sensor selection approach in accordance with some embodiments.

FIG. 5E illustrates an exemplary sensor 105 selection approach in accordance with some embodiments. In the exemplary embodiment shown in FIG. 5E, a respective selector element 111 (e.g., shown as a CMOS transistor) is coupled in series with the sensor 105. In this exemplary embodiment, three lines 120A, 120B, and 120C allow a characteristic of the sensor 105 to be sensed. Conceptually, the line 120A may be considered to be a read-out line, the line 120C may be considered to be a control line, and the line 120B may be considered to be either or both a read-out line and a control line. For more detail on configurations such as the exemplary one shown in FIG. 5E, see B. N. Engel, J. Akerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAIVI Based on a Novel Bit and Switching Method," IEEE Transactions on Magnetics, Vol. 41, 132 (2005).

Figure 5F:
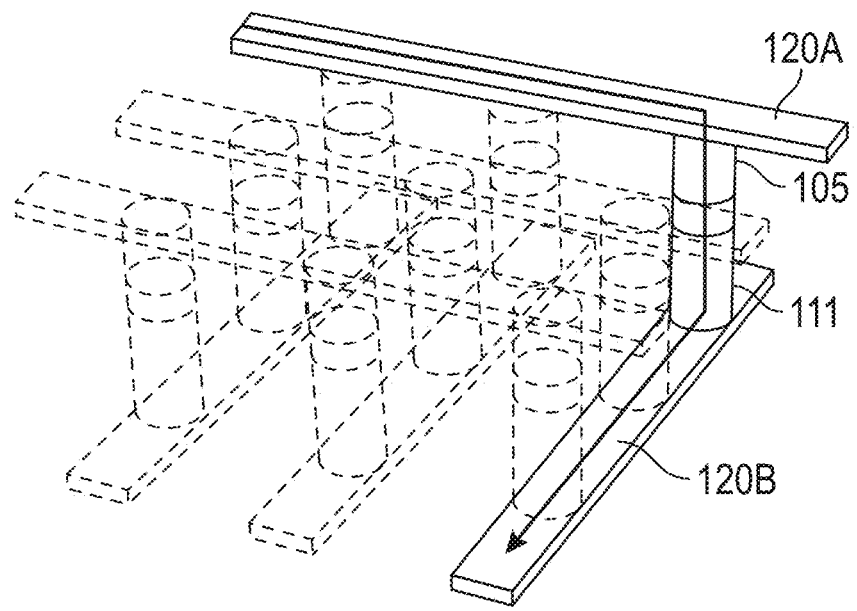
FIG. 5F illustrates another sensor selection approach in accordance with some embodiments.

FIG. 5F illustrates another exemplary sensor 105 selection approach in accordance with some embodiments. In the exemplary embodiment shown in FIG. 5F, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with the magnetic films of the sensors 105 and then placed into a cross-point architecture. Although FIG. 5F shows the in-stack selector elements 111 below the sensors 105, it is to be understood that the order of the in-stack selector elements 111 and the sensors 105 may be reversed. Respective selector devices (e.g., CMOS transistors) may be used to turn on the individual lines 120A, 120B to address/access individual sensors 105 in the detection device 100. The use of CMOS select transistors may be simple due to the prevalence of foundries available to fabricate the front end (i.e., the nanofabrication to build the CMOS transistors and underlying circuitry), but the types of currents used for operation may use a cross-point design to eventually reach the densities desired. Additional details on configurations suitable to select sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

FIGS. 6A through 6C illustrate an embodiment of a cross-point array architecture 300 that may be included in the detection device 100 in accordance with some embodiments. For illustration, the sensors 105 illustrated in FIGS. 6A through 6C comprise MTJ elements 308, but it is to be appreciated that, as explained above, some or all of the sensors 105 may be spin valves.

Referring to FIG. 6A, the cross-point array architecture 300 includes top wires 318 and bottom wires 320. As shown in the exemplary embodiment of FIG. 6A, the top wires 318 are oriented substantially perpendicularly to (at approximately 90 degree angles from) the bottom wires 320. An example MTJ element 308 (e.g., a sensor 105) is situated between a crossing of the array (dashed circle). The example MTJ element 308 includes two or more FM layers 310, 314 separated by one or more non-magnetic layers 107 (e.g., comprising MgO). As shown, one of the FM layers is a free layer 310 that will rotate in the presence of a magnetic field, and another of the FM layers is a pinned (or fixed) layer 314 that may be a single FM layer coupled to an AFM layer 312. Alternatively, a compound structure called a synthetic antiferromagnet (SAF) may be used. The SAF includes two FM layers separated by a magnetic coupling layer (e.g., ruthenium), with one of the two FM layers coupled to an AFM layer. It is to be understood that although the example layer arrangement of MTJ element 308 shows a general structure with layers over or under other layers, intervening layers not shown can be inserted. Moreover, as discussed above, additional layers may be disposed above and/or below the illustrated structure.

To illustrate some of the features of the cross-point array architecture 300, FIG. 6B shows a cross-section of the cross-point array architecture 300 along the top wire 318 direction (indicated in FIG. 6A by the dash-dot line labeled "6B"), and FIG. 6C shows a cross-section of the cross-point array architecture 300 along the bottom wire 320 direction (indicated in FIG. 6A by the dashed line labeled "6C"). As shown, the sides of the MTJ elements 308 (the sensors 105) are encapsulated by material 336, which may be an insulator. Optionally, as shown in FIG. 6B, a hard bias magnetic material 338 may also be deposited between the MTJ elements 308. In embodiments including hard bias magnetic material 338, a thin layer of insulator 340 is also deposited on top of the hard bias magnetic material 338 to electrically insulate it from the top wire(s) 318.

Referring to FIG. 6C, the cross section shows the fluidic channels 115 (e.g., nanofluidic or microfluidic channels), which may be, for example, trenches etched in an insulator. As shown, a small amount of insulator 322 is left on the sidewalls of the sensors 105 (illustrated as MTJ elements 308) so that the MNPs do not electrically interact with the sensors 105. The portion of the insulator exposed to (and forming) the fluidic channel 115 may form the wall 117 to which polymerase molecules or molecules to be detected (e.g., nucleic acid samples) may be attached for detection.

Detection Circuits

Determining the state of the sensor 105 (e.g., determining whether the STO is oscillating, determining whether it is oscillating at a particular frequency or within a particular frequency band, determining at what frequency the STO is oscillating, etc.) can be accomplished using various types of detection circuitry.

In some embodiments, determining the state of the sensor 105 is accomplished using a super-heterodyne detection circuit. Generally, super-heterodyne detection may be used to detect RF signals using a frequency mixing technique that takes a high frequency signal and "down-shifts" it to a much lower frequency (e.g., baseband or an intermediate frequency) at which the signal can be processed more conveniently. This method involves the use of a non-linear mixer element that adds alternating current (AC) voltage signals with the functional form $V_n \sin(\omega_n t)$, where $V_n$ and $\omega_n$ are the peak voltage and frequency, respectively, of the nth signal. To understand the behavior of this element, consider the output $V_{mix}$ of a mixer to be a function of two input signals:

$$V_{mix} = F(V_1 \sin(\omega_1 t) + V_2 \sin(\omega_2 t))$$

Because the mixer is a non-linear element, expanding the summation in a power series produces the expression:

$$V_{mix} = \alpha_1(V_1 \sin(\omega_1 t) + V_2 \sin(\omega_2 t)) + \alpha_2(V_1^2(\sin(\omega_1 t))^2 + 2V_1V_2 \sin((\omega_2 t) + V_2^2(\sin(\omega_2 t))^2) + \ldots$$

where terms higher than second order are ignored. Using the trigonometric identities $\sin^2(x) = \frac{1}{2}(1 - \cos(2x))$ and $2 \sin(\omega_1 t)\sin(\omega_2 t) = \cos(\omega_1 t - \omega_2 t) - \cos(\omega_1 t + \omega_2 t)$, the equation above may be simplified into the form:

$$V_{mix} = \alpha_1(V_1 \sin(\omega_1 t) V_2 \sin(\omega_2 t)) + \alpha_2 \left( \frac{V_1^2}{2}[1 - \cos 2\omega_1 t] + V_1 V_2 [\cos(\omega_1 - \omega_2)t - \cos((\omega_1 + \omega_2)t)] + \frac{V_2^2}{2}[1 - \cos 2\omega_2 t] \right) + \ldots$$

Ignoring the higher-frequency terms, the mixed signal now consists of terms with frequencies that are the difference and sum of the original input signal frequencies:

$$V_{mix} = \alpha_2 V_1 V_2 \cos(\omega_1 - \omega_2)t - \alpha_2 V_1 V_2 \cos(\omega_1 + \omega_2)t +$$

Figure 7A:
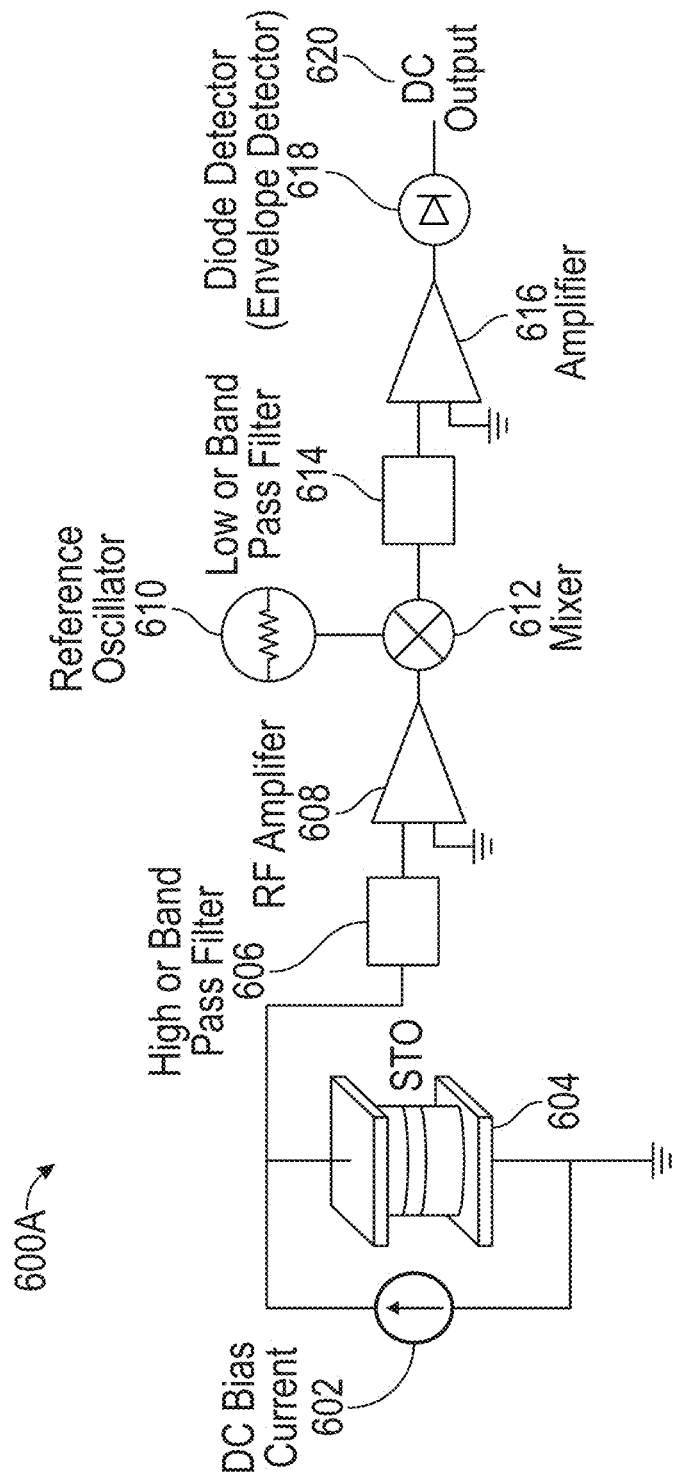
FIG. 7A illustrates an exemplary super-heterodyne circuit for molecule detection in accordance with some embodiments.

FIG. 7A illustrates an exemplary super-heterodyne detection circuit 600A in accordance with some embodiments. In the illustrated embodiment, a STO 604 generates a RF signal (e.g., in response to a magnetic field generated by a MNP in its vicinity) when the DC bias current 602 is applied. The frequency of the RF signal generated by the STO 604 (e.g., in response to the presence or absence of a selected MNP type) can be selected/designed through the choice of materials, dimensions, amplitude of the applied DC bias current 602, magnetic field, and other variables, as is known in the art.

In the exemplary embodiment of FIG. 7A, the RF signal (e.g., in the range of 1-10 GHz) from the STO 604 is first passed through a high-pass or band-pass filter 606 to substantially eliminate from the RF signal any DC signal from the DC bias current 602 used to excite the STO 604. Assuming the STO 604 oscillates at a known frequency with small variation, a band-pass filter with the band centered around the STO's oscillation frequency may be used to reduce noise and improve the signal-to-noise ratio (SNR). A high-pass filter may be used, for example, if the STO 604's frequency variation is large and/or there are large variations of the STO 604's frequency over the sensor array 110 (e.g., as shown in FIGS. 4A-4C, 5A-5D, etc.).

As shown in FIG. 7A, the output from the filter 606, which may be on the order of pico- to nano-Watts of power, is optionally amplified by a RF amplifier 608 and sent to a mixer 612, where a fixed-reference signal from a reference oscillator 610 is used to mix the output down to, for example, frequencies below 100 MHz. The reference oscillator 610 may produce a reference signal having a frequency close to that of the STO 604. Alternatively, instead of a reference oscillator 610, the source of the reference signal can be a reference STO 604 (e.g., substantially identical to the STOs 604 of the sensors 105 in the sensor array 110, but removed from the fluidic channel(s) 115 and physically separated from the sensor array 110) or any other element that generates a high-frequency signal at a frequency approximately equal to the frequency of the signal expected to be generated by the STO 604. For example, ring oscillators or other signal generators used in very-large-scale integration (VLSI) designs may be suitable.

In the exemplary embodiment illustrated in FIG. 7A, the output of the mixer 612 is then passed through a low-pass or band-pass filter 614 to remove higher-frequency components. As shown in FIG. 7A, the output signal from the low-pass or band-pass filter 614 may optionally be amplified by a second amplifier 616. The output signal is then passed to a diode detector circuit 618 (or, e.g., any other suitable circuit that operates as an envelope detector), and the envelope of the output signal may be detected as a DC voltage (output 620).

As will be appreciated by those having ordinary skill in the art, in the exemplary embodiment of FIG. 7A, if there is no input RF signal at the input to the RF amplifier 608, the output of the mixer 612 ($\omega_1 - \omega_2$) will also be approximately zero. Accordingly, the output of the circuit 600A will be a DC voltage only when the frequency of the RF signal generated by the STO 604 approximately matches the frequency of the signal generated by the reference oscillator 610. Thus, the response of the exemplary super-heterodyne detection circuit 600A to the STO 604 changing from being "on" to being "off" would be to go from a finite measured voltage to (approximately) zero volts. In other words, the presence of a non-zero DC output 620 indicates that the STO 604 is "on," whereas an absence of a DC output 620 (or a DC output 620 below a threshold) indicates that the STO 604 is "off."

It is to be understood that another mode of operation of the exemplary super-heterodyne detection circuit 600A is achieved if the STO 604 does not "turn off" in response to the presence (or absence) of a MNP in its vicinity, but instead has its frequency altered sufficiently due to the field from a MNP such that ($\omega_1 - \omega_2$) is larger than the cutoff frequency of the low/band-pass filter 614, which would also result in (approximately) no signal at the DC output 620. In either approach, detecting the presence (or absence) of a MNP label (e.g., tethered to a DNA base (or to an incorporated nucleotide precursor)) can be a binary operation where the detection circuitry 130 detects an output voltage in the absence of a MNP in the vicinity of a sensor 105 and no signal when a NMP is present (or vice versa). This approach allows for rapid evaluation of the presence or absence of MNPs in a large area array 110 of sensors 105 comprising STOs 604, which can boost the throughput of a detection system (e.g., for DNA sequencing applications) and increase the speed of data collection.

As explained previously, some embodiments allow for the detection of different MNP types, each of which has a distinguishable effect on the oscillation of the STO 604. For example, a first MNP type may cause the STO 604 to oscillate at a first frequency, a second MNP type may cause the STO 604 to oscillate at a second frequency, a third MNP type may cause the STO 604 to oscillate at a third frequency, and a fourth MNP type may cause the STO 604 to oscillate at a fourth frequency. In some such embodiments, the reference oscillator 610 shown in FIG. 7A may be tunable such that the frequency of the signal generated by the reference oscillator 610 may be, at various times, at or around any of the first, second, third, and fourth frequencies.

Figure 7B:
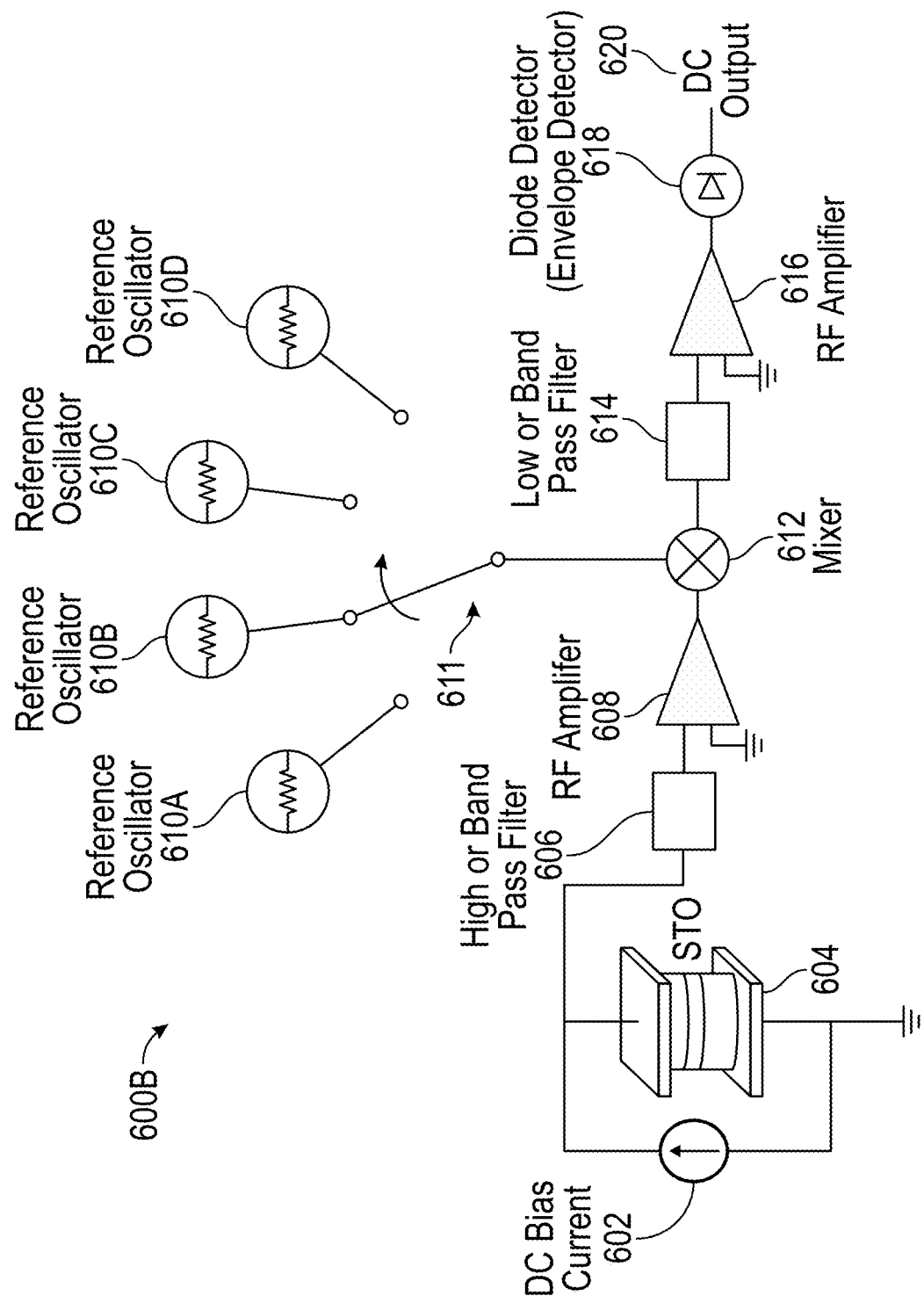
FIG. 7B illustrates another exemplary super-heterodyne circuit for molecule detection in accordance with some embodiments.

Alternatively, the exemplary circuit 600A may be modified as shown in FIG. 7B, in which the single reference oscillator 610 has been replaced by a set of four reference oscillators, 610A, 610B, 610C, and 610D coupled to a switch 611. The circuit 600B of FIG. 7B may be used in a DNA sequencing application in which each nucleotide precursor is labeled by a different MNP type, with each MNP type causing the STO 604 to generate a RF signal having a different frequency (e.g., a first MNP type causes the STO 604 to oscillate at a first frequency, a second MNP type causes the STO 604 to oscillate at a second frequency, a third MNP type causes the STO 604 to oscillate at a third frequency, and a fourth MNP type causes the STO 604 to oscillate at a fourth frequency). After all four MNP-labeled nucleotide precursors have been introduced into the fluidic channel 115 of a sequencing device, and enough time has elapsed for incorporation, the switch 611 may be activated to, in turn, connect each of the reference oscillators 610A, 610B, 610C, and 610D to the mixer 612. The DC output 620 of the circuit 600B should be nonzero only when the reference oscillator 610 associated with the MNP type labeling the incorporated nucleotide precursor is connected to the mixer 612. For example, if the reference oscillator 610A generates a reference signal at a first frequency that is approximately the same as the expected frequency at which the STO 604 will oscillate in the presence of the first MNP type, and the DC output 620 is nonzero when the switch 611 connects the reference oscillator 610A to the mixer 612, it can be deduced that the incorporated nucleotide precursor is the one labeled by the first MNP type.

In some embodiments having multiple reference oscillators 610 (e.g., FIG. 7B) or a tunable single reference oscillator 610, the low- or band-pass filer 614 is a low-pass filter having a cutoff frequency higher than the highest of the first, second, third, and fourth frequencies. In other embodiments, the low- or band-pass filter 614 is a tunable band-pass filter that can be tuned so that its passband approximately centers, at different times, on the first, second, third, and fourth frequencies and, so centered, does not overlap any of the other of the first, second, third, or fourth frequencies.

In some embodiments, the STOs 604 are designed to generate RF signals characterized by a large change in frequency due to the magnetic field generated by the MNPs. Here, the STOs 604 can also be considered to turn either "off" or "on" depending on the choice of reference oscillator 610 frequency used in the detection circuits described above. For example, referring to FIG. 7A, if, at equilibrium (i.e., when no MNP is present), the frequency of the signals generated by the STOs 604 is $f_1$ and the reference oscillator 610 frequency is $f_0 \approx f_1$, the frequency of the signal at the output of the mixer 612, namely $(f_1-f_0)$, will be smaller than the cutoff frequency of the low-pass (or band-pass) filter 614 prior to the diode detector 618. A finite voltage can then be read at the output of the circuit 600A. When a MNP is present and exerting an additional magnetic field on the STO 604, the frequency of the STO 604 changes to $f_2$, which is either much larger or smaller than $f_0$. As a result, the output of the mixer 612 is strongly attenuated by the low-pass (or band-pass) filter 614, because the signal frequency is (much) higher than the filter 614's cutoff frequency. Then the output of the detector circuit 600A is effectively zero, as in the case described above, without any requirement for a tight band of magnetic field in which STO oscillations occur. It should be noted that once again the response can be reversed by choosing the reference oscillator 610 frequency to be different from the STO 604 frequency at equilibrium and set to be close to the STO 604 frequency in the presence of a MNP, so that a signal is only detected in the presence of a particle.

Note that although FIGS. 7A and 7B show a single STO 604 at the input of the super-heterodyne circuit 600A, 600B, in other embodiments an ensemble of STOs 604 provides the input into a single detector circuit 600A, 600B using, for example, multiplexers. Such embodiments can reduce the footprint consumed by the detection circuitry 130 on a detection device 100 (e.g., a microfluidic chip used for sequencing of nucleic acids). Also envisioned is a separate circuit board or chip to handle super-heterodyne detection within a detection system, although this approach may increase the latency of the system as well as use signal amplification (e.g., RF amplifier 608 and/or amplifier 616 shown in FIGS. 7A and 7B), which might not be used if the circuit 600A, 600B is included on the detection device 100 itself (e.g., a DNA sequencing chip).

Figure 8A:
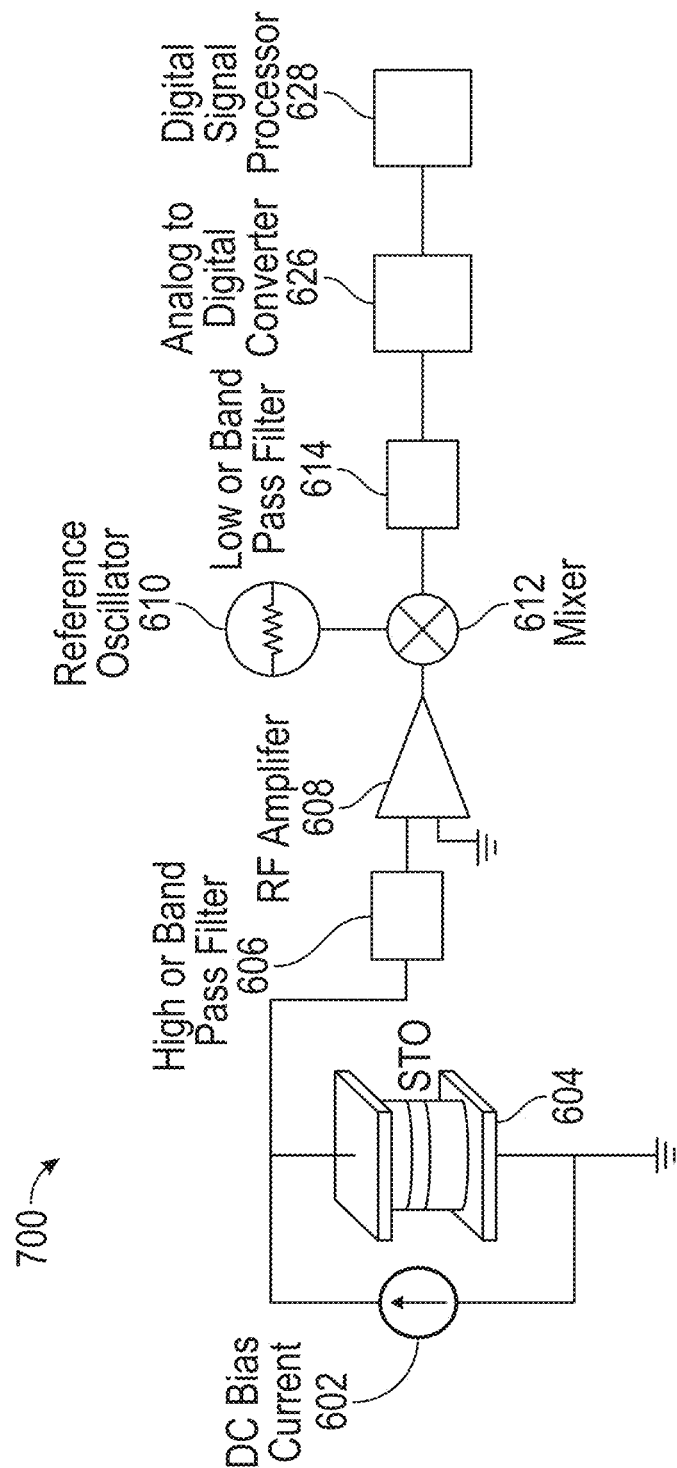
FIGS. 8A and 8B illustrate exemplary detection circuits including analog-to-digital converters (ADCs) in accordance with some embodiments.
Figure 8B:
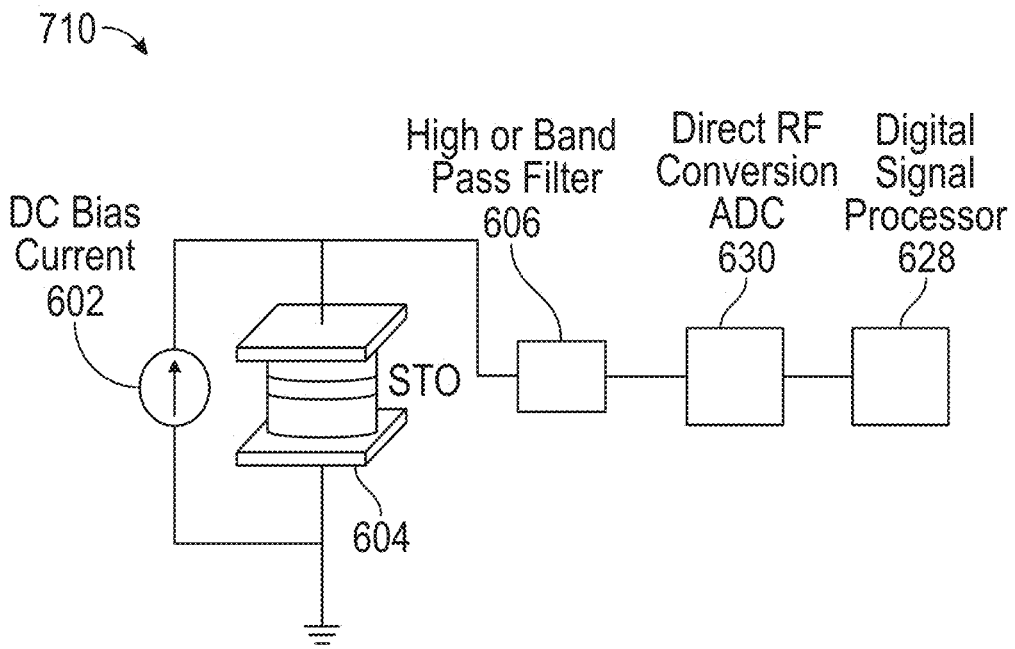

FIGS. 8A, 8B, 9, and 10 show additional and/or alternative exemplary detection circuitry 130 embodiments for detecting the frequency and/or presence/absence of a signal generated by a STO 604 in accordance with some embodiments. FIGS. 8A and 8B show two alternative analog-to-digital converter (ADC)-based embodiments. Several of the elements of FIGS. 8A and 8B are identical to those shown in FIGS. 7A and 7B and have identical reference numbers. Those elements were described above, and that discussion applies in the context of FIGS. 8A and 8B and is not repeated.

The detection circuit 700 of FIG. 8A differs from that of FIGS. 7A and 7B in that digital, rather than analog, signal processing is used. Specifically, as shown, the output from the low- or band-pass filter 614 is provided as the input to an ADC 626. The output of the ADC 626 is provided to a digital signal processor (DSP) 628, which can then detect the frequency of the RF signal using known methods (e.g., by calculating a fast Fourier transform or by applying any other known frequency-analysis technique to assess the frequency content of the RF signal, etc.). It is to be understood that although FIG. 8A and other figures herein illustrate a DSP 628, other components could be used in addition or instead. For example, the DSP 628 can be augmented or replaced by components such as a general-purpose processor, an application-specific integrated circuit (IC), a microprocessor, a controller, a programmable logic device, a field-programmable gate array, or other similar components that are known in the art. Furthermore, although FIG. 8A illustrates many of the same components as FIGS. 7A and 7B, several of these components are optional. For example, the high- or band-pass filter 606, reference oscillator 610, mixer 612, and low- or band-pass filter 614 are optional, and one or more of them may be omitted from FIG. 8A. As will be appreciated by those having ordinary skill in the art, with the optional mixer 612 and optional reference oscillator 610 omitted, FIG. 8A allows the frequency of the RF signal generated by the STO 604 to be detected/measured digitally. For example, the DSP 628 may perform a Fourier transform (or any other technique to assess the frequency content of the signal) and identify peaks in the frequency spectrum. The location(s) of the peak(s) may then be assessed in view of the expected RF signal frequencies of the MNP types being used to identify which, if any, of the MNP types has been detected.

The detection circuit 710 in FIG. 8B is another digital approach that uses direct RF conversion. In this exemplary embodiment, the output of the high- or band-pass filter 606 is the input to a direct RF conversion ADC 630 operating at a high frequency (sampling rate) and with a relatively small bandwidth. The output of the direct RF conversion ADC 630 is provided to a DSP 628, which may then detect the frequency of the RF signal generated by the STO 604 using known methods (e.g., by calculating a fast Fourier transform or by applying any other known frequency-analysis technique to assess the frequency content of the RF signal, etc.). This embodiment may be advantageous in some applications because the ADC 630 and DSP 628 process the signal without downconversion (e.g., the ADC 630 and DSP 628 process the signal at the RF signal frequency generated by the STO 604). It is noted that in the exemplary embodiment of FIG. 8B, the use of an anti-aliasing filter is optional due to the limited bandwidth of the STO 604. Optionally, the detection circuit 710 may additionally include a low noise amplifier.

Figure 9:
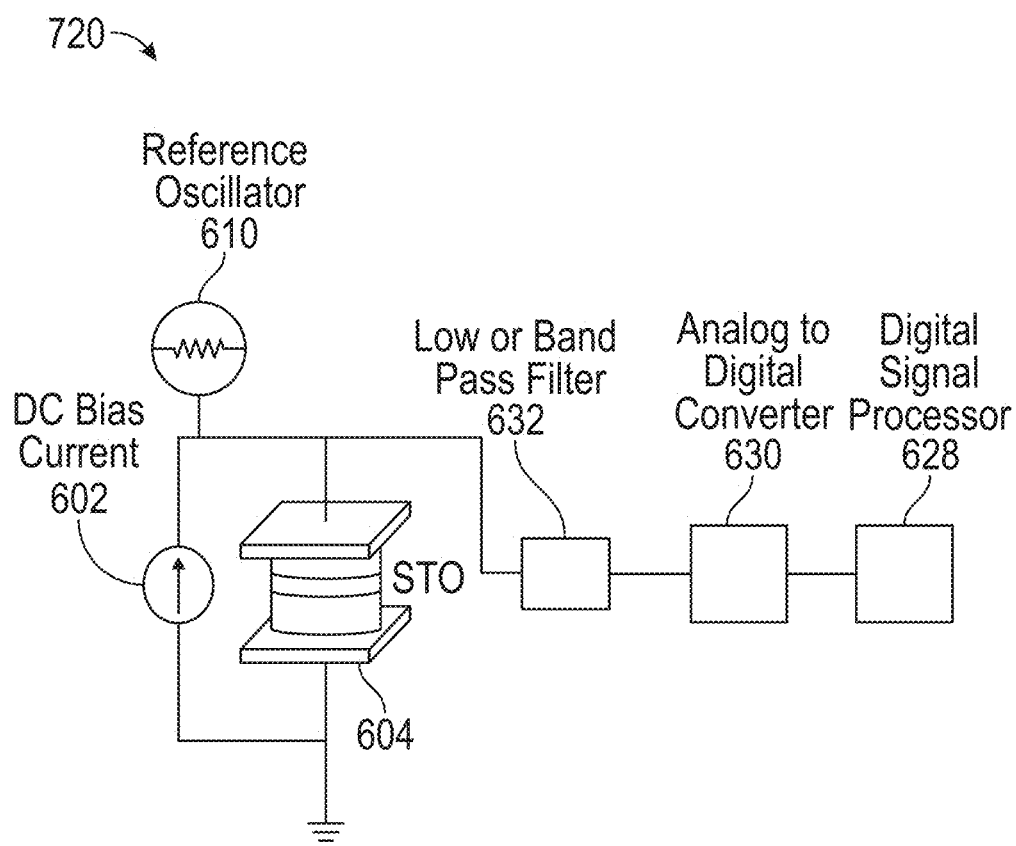
FIG. 9 illustrates an exemplary in-sensor mixing circuit in accordance with some embodiments.

FIG. 9 shows an exemplary in-sensor mixing circuit 720 for use in accordance with some embodiments. In other words, at least a portion of the circuit 720 may be incorporated into the sensor 105. The circuit 720 of FIG. 9 is similar to the circuit 710 of FIG. 8B, except that in FIG. 9 a reference oscillator 610 is coupled with the STO 604 before the low or band-pass filter 632. It is to be understood that although FIG. 9 shows an embodiment that uses digital processing, use of in-sensor mixing is also contemplated for purely analog detection embodiments such as those shown in FIGS. 7A and 7B.

Figure 10:
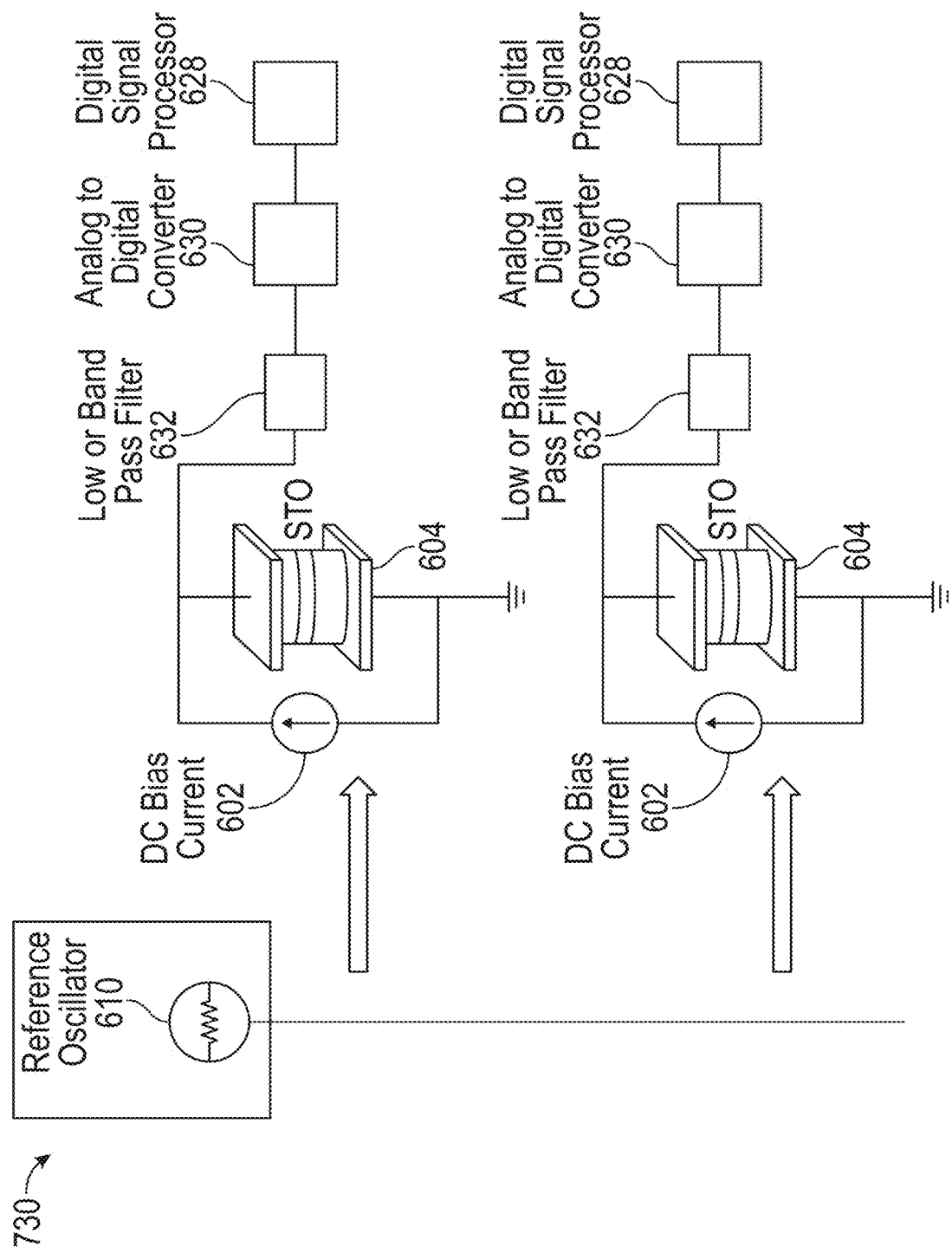
FIG. 10 illustrates an exemplary parallel array operation detection circuit in which a reference oscillator is coupled to multiple STOs in accordance with some embodiments.

FIG. 10 shows another detection circuit 730 in accordance with some embodiments. The circuit 730 is a parallel array operation embodiment in which a single reference oscillator 610 is coupled to two or more STOs 604 and their associated detection circuits. The exemplary circuit 730 of FIG. 10 further extends the concept of FIG. 9 so that the reference oscillator 610 is shared among two or more STOs 604 and their associated circuitries. It is to be appreciated that the embodiments of FIGS. 9 and 10 can also be adapted to operate with the configurations shown in FIGS. 7A and 7B.

In addition to one or more of the circuits described in the context of FIGS. 7A-10, as described above, the detection circuitry 130 may include, for example, a processor configured to execute machine-executable instructions enabling the processor to interpret the meaning of the output of the circuit. In some embodiments in which the output of the circuit is an analog signal (e.g., FIG. 7A, FIG. 7B), the detection circuitry 130 may include an analog-to-digital converter disposed between the output of the circuit 600A, 600B and a processor.

Detection Methods

The sensors 105 and/or detection devices 100 described above may be used to detect molecules labeled by MNPs, as described further below. Suitable detection methods include those in which a binary decision (e.g., yes/no, 1/0, etc.) is made as to whether a MNP, and therefore a molecule to which the MNP is coupled, is present in the vicinity of a sensor 105. For simplicity, the explanation below is presented in the context of DNA sequencing, but, as stated previously, it is to be understood that the methods described also may be used in other applications and to detect types of molecules other than nucleic acids.

In some embodiments, target molecules to be detected (e.g., nucleic acid strands to be sequenced) are attached to the walls 117 of the fluidic channel(s) 115 of a detection device 100. Polymerase may be introduced at this point. For example, the polymerase may be bound (attached or coupled) to the wall 117 along with a target ssDNA to be sequenced. Nucleotide precursors labeled by MNPs may then be introduced into the fluidic channel(s) 115. The polymerase operates to incorporate complementary nucleotide precursors labeled by MNPs into the target DNA strand. Only the appropriate (complementary) base (i.e., for DNA sequencing, cytosine (C) with guanine (G) or adenine (A) with thymine (T)) will be incorporated, and its presence can be detected by the sensors 105. Assuming this process is done one base pair at a time, the presence or absence of the MNP labeling the complementary nucleotide precursor, and therefore the identity of base with which that nucleotide precursor pairs in the target DNA strand, can be determined using the various device embodiments of, for example, FIGS. 4A-5F.

The presence or absence of a MNP in the vicinity of a particular sensor 105 can be detected by applying a magnetic field across the sensor 105 and applying a bias current to read the sensor 105. The application of a magnetic field across the sensor 105 is optional, but it may be beneficial in applications in which multiple types of MNPs are present (e.g., in DNA sequencing applications in which different nucleotide precursors are labeled by different MNP types and multiple nucleotide precursors are added to the fluidic channel 115 at substantially the same time). The magnetic field may be applied using an electromagnet, e.g., by placing the pole pieces on either side of the detection device), a distributed coil, a solenoid oriented perpendicular to the fluidic channel 115, etc. to generate the magnetic field in the direction of the pinned layer 314's moment. The means for generating the magnetic field may be mounted, for example, on the bottom surface 119 of the detection device 100. As another example, the means for generating a magnetic field may be included in a system that includes the detection device 100. It is to be understood that other suitable means of generating the magnetic field, such as, for example, by using permanent magnets or super-conducting magnets, are possible, are specifically contemplated herein, and are not excluded. The applied magnetic field aligns the moments of all of the MNPs in a common direction so that the measured signals due to the presence of a MNP are similar.

With the free layer excited through spin transfer effects and the fixed layer with its moment fixed, a STO excited as described above (e.g., in the context of FIG. 3C) will produce a RF voltage signal from an applied DC current due to resistance fluctuations caused by magnetoresistive effects. Therefore, by connecting the sensors 105 to detection electronics/circuitry as described above, the presence and/or absence of MNPs near the sensors 105 can be detected. In DNA sequencing applications, for example, nucleotide precursors (or, more generally, nucleic acids) labeled by MNPs and incorporated into a target DNA strand by polymerase may be detected by determining whether the sensor 105 is generating a RF signal (e.g., at a specified frequency or within a specified frequency band), because only in the presence of a MNP labeling the nucleotide precursor incorporated in a target DNA strand being sequenced would the local magnetic field be sufficient to "turn on" (or "turn off," or shift the oscillation frequency of) the STO.

Figure 11:
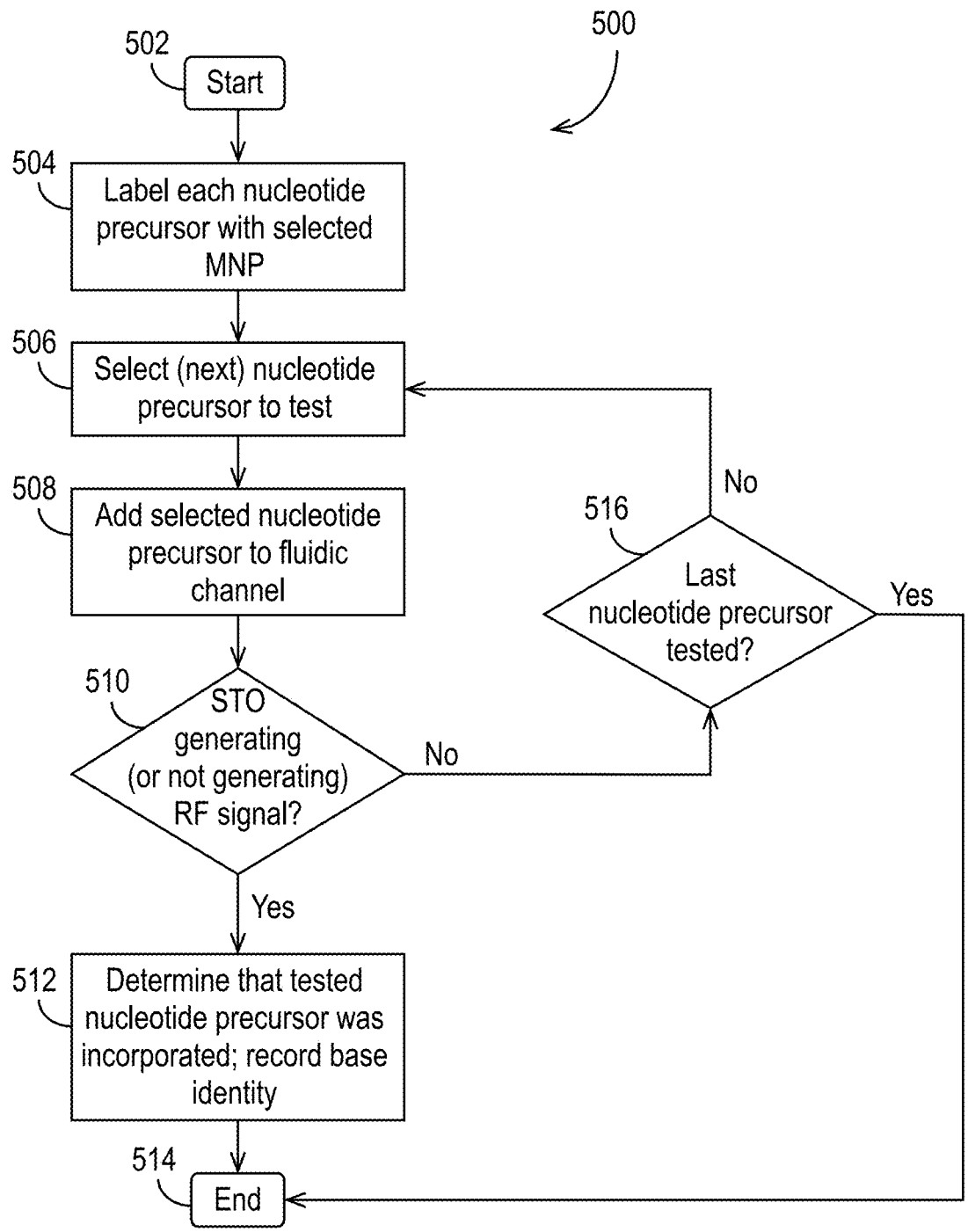
FIG. 11 illustrates an exemplary method suitable for DNA sequencing using a single MNP type in accordance with some embodiments.

Methods of molecule detection may use a single MNP type or multiple MNP types. FIG. 11 illustrates an exemplary sequential binary method 500 suitable for DNA sequencing in which a single MNP type is used to label all four nucleotide precursors in accordance with some embodiments. FIG. 11 is applicable whether the presence of a MNP in the vicinity of a sensor 105 causes the STO to "turn on" or "turn off." It is to be understood that FIG. 11 illustrates the procedure for a single sensor 105. In embodiments in which a detection device 100 includes a plurality of sensors 105, some of the steps of the method 500 (e.g., steps 510, 512, 514) may be performed independently for each of the plurality of sensors 105.

At 502, the method 500 begins. At 504, molecules of each the four nucleotide precursors (A, T, C, and G) are all labeled by the same type of MNP. The different nucleotide precursors, each labeled by the same MNP type, are then introduced one at a time into, for example, a fluidic channel 115 of a detection device 100. Thus, at 506, a first nucleotide precursor to be tested is selected. At 508, the selected (magnetically-labeled) nucleotide precursor is added to the fluidic channel 115 of a detection device 100. After sufficient time has passed to allow the nucleotide precursor to be incorporated in the target DNA strands being sequenced, at 510, it is determined whether the STO of a selected sensor 105 is, or is not, generating a RF signal having specified characteristics. The characteristics may include, for example, an amplitude and/or frequency.

As explained above, in some embodiments, the STO generates the RF signal in response to one or more MNPs being in its vicinity but otherwise does not generate the RF signal. In such embodiments, the presence of one or more MNPs causes the STO to "turn on." In other embodiments, the STO generates the RF signal in the ordinary course and ceases to generate it in response to one or more MNPs being in its vicinity. In such embodiments, the presence of one or more MNPs causes the STO to "turn off." The presence or absence of the RF signal caused by the presence or absence one or more MNPs can be detected using suitable detection circuitry 130, including, for example, the exemplary embodiments described above in the context of FIGS. 5E, 5F, and 7A-10.

In embodiments in which MNPs cause the STO to "turn on" (the presence of the RF signal indicates the presence of one or more MNPs in the vicinity of the sensor 105), if it is determined at 510 that the STO of the selected sensor 105 is generating a RF signal having the specified characteristics, then at 512 it is determined that the tested nucleotide precursor was incorporated into a DNA strand coupled to a binding site associated with the sensor 105. The identity of the base with which the tested nucleotide precursor paired (its complement) may then be recorded. If, however, is it determined at 510 that the STO of the selected sensor 105 is not generating a RF signal having the specified characteristics (interpreted to mean that the previously-tested nucleotide precursor was not incorporated at the binding site associated with the sensor 105), then at 516 it is determined whether the previously-tested nucleotide precursor was the last of the four nucleotide precursors to be tested. If so, then the method ends at 514. If not, the method returns to 506, where the next nucleotide precursor to be tested is selected, and at least steps 508 and 510 are repeated.

In embodiments in which the MNPs cause the STO to "turn off" (the absence of the RF signal indicates the presence of one or more MNPs in the vicinity of the sensor 105), if it is determined at 510 that the STO of the selected sensor 105 is not generating a RF signal having the specified characteristics, then at 512 it is determined that the tested nucleotide precursor was incorporated into a DNA strand coupled to a binding site associated with the sensor 105. The identity of the base with which the tested nucleotide precursor paired (its complement) may then be recorded. If, however, it is determined at 510 that the STO of the selected sensor 105 is generating a RF signal having the specified characteristics (interpreted to mean that the previously-tested nucleotide precursor was not incorporated at the binding site associated with the sensor 105), then at 516 it is determined whether the previously-tested nucleotide precursor was the last of the four nucleotide precursors to be tested. If so, then the method ends at 514. (Again, it is to be understood that when a detection device 100 includes a plurality of sensors 105, the method 500 may end for some sensor(s) 105 but not for others if the DNA fragments being sequenced are not identical and the base pair to be completed and detected by different sensors 105 differs.) If not, the method returns to 506, where the next nucleotide precursor to be tested is selected, and at least steps 508 and 510 are repeated.

The method 500 can be performed using one or more sensors 105. It is to be appreciated that when more than one sensor 105 is used, the decision at 510 can differ for different sensors 105. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and TTAG) as well as, if a plurality of the longer strands are cut into sub-strands, sub-strands that partially or completely overlap other sub-strands (e.g., GGCTTA and TTAG). All of the smaller, randomized sub-strands may be sequenced at the same time, potentially after being amplified. In such applications, it will be appreciated that because the sub-strands do not represent the same sub-sequences, it may be desirable to detect RF signals generated (or not generated) by each sensor 105 to detect MNPs because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP type has been incorporated. Accordingly, when using the exemplary method 500 shown in FIG. 11, the decision at 510 may be "yes" for one sensor 105 after addition of a particular nucleotide precursor and "no" for another. Thus, when sequencing randomized sub-strands of a nucleic acid such as DNA, it may be desirable to test all four nucleotide precursors during each sequencing cycle, even though for some of the sensors 105 the decision at 510 is "yes" for the first, second, or third tested nucleotide precursor.

Although FIG. 11 assumes that each of the nucleotide precursors is labeled by the same type of MNP, it is not a requirement to use the same type of MNP for each of the nucleotide precursors. For example, it may be convenient to use the same type of MNP for each of the nucleotide precursors, but, alternatively, different nucleotide precursors may be labeled by different types of MNP. In other words, two or more of the nucleotide precursors may be labeled by the same type of MNP, or two or more nucleotide precursors may be labeled by different types of MNP.

For example, various other embodiments are directed to using multiple MNP types (for example, MNP 1, 2, 3, and 4), each causing the sensor 105 to generate a distinguishable RF signal. Focusing on the DNA example for illustration, each individual base (A, T, C, G) can be labeled by a different type of MNP (e.g., base A with MNP 1, base C with MNP 2, base G with MNP 3, and base T with MNP 4) by either tagging each base separately and mixing them together or functionalizing each type of MNP differently so that it has an affinity for a particular (e.g., its assigned) base. In a single chemistry run, all tagged (magnetically-labeled) bases may be introduced into a microfluidic cell (e.g., the fluidic channel 115 of the detection device 100) in which DNA strands (e.g., fragments) to be sequenced have been attached within the microfluidic cell (e.g., as described in the discussion above of the detection devices 100).

After binding the target DNA strands to be sequenced to the detection device 100, all four magnetically-labeled nucleotide precursors can be introduced into the fluidic channel at the same time. Polymerase acts to incorporate nucleotide precursors that are complementary to those in the target strand. Changes in RF signals generated (or not generated) by STOs of the detection device 100 can be used to identify which MNP (and, therefore, nucleotide precursor), if any, has been incorporated in the vicinity of each sensor 105. After each nucleotide precursor has been introduced in the fluidic channel(s) 115, and the sensors 105 have been read, the MNPs may be cleaved from the incorporated magnetically-labeled nucleotide precursor using, for example, enzymatic or chemical cleavage, as is known in the art. The process can then be repeated for the next unpaired base in the strand being sequenced.

Accordingly, in some embodiments for DNA sequencing applications, instead of using a binary method with four chemistry steps for each base read (sequencing cycle), four different MNPs, each causing the STO to generate a distinguishable RF signal, can be used as the magnetic labels, and all of them can be detected in a single chemistry step. For example, each type of molecule (e.g., in DNA sequencing applications, each dNTP type) can be labeled by a different MNP type, where each MNP type causes the STO to generate (or not generate) a RF signal having at least one characteristic (e.g., frequency) enabling the presence or absence of the MNP to be distinguished from all other MNPs being used as magnetic labels. For example, in a DNA sequencing application, A can be labeled by MNP1, T by MNP2, C by MNP3, and G by MNP4, where the frequencies of the RF signals generated by STOs influenced by MNP1, MNP2, MNP3, and MNP4 are all different enough that the three or four types of MNPs can be distinguished by detecting whether the STO is generating (or has ceased to generate) a RF signal having specified characteristics (e.g., frequency). Detection circuitry 130 (e.g., exemplary embodiments shown and described in the context of FIGS. 7A-10) can detect the frequency (or change in frequency) of the RF signal generated by each STO to identify which of the nucleotide precursors has been incorporated into the DNA strand bound in the vicinity of and associated with that STO.

For example, as explained above (see, e.g., the discussion of FIG. 7A), the detection circuitry 130 may include a tunable reference oscillator (RO) 610, and the detection circuitry 130 may sweep the frequency range of the RO 610 while measuring the STO signal. When the RO 610 frequency is close to the STO frequency (e.g., using the circuit 600A of FIG. 7A), the DC output 620 is nonzero. It can be determined based on the nonzero DC output 620 and the frequency of the RO 610 when the DC output 620 is nonzero what the frequency of the STO signal is. Knowing how the STO frequency changes due to the magnetic fields emitted by the different MNPs being used as labels, it can be determined which particle is present.

Figure 12A:
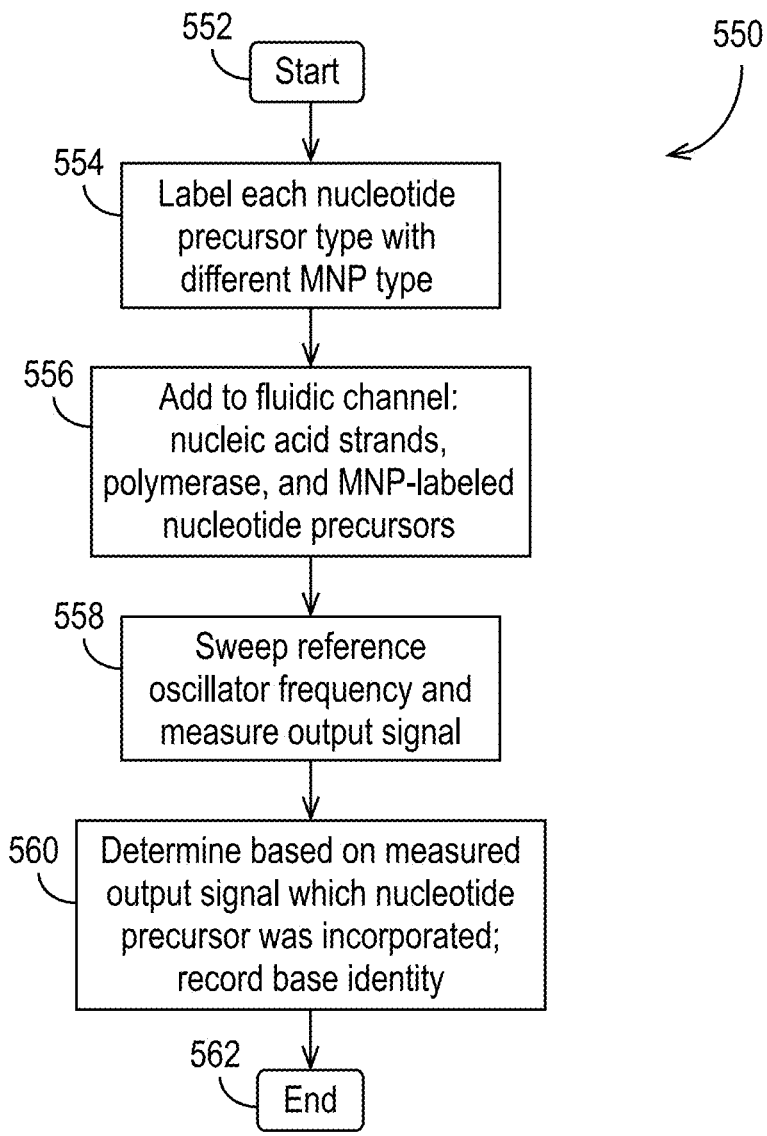
FIG. 12A illustrates a method suitable for DNA sequencing using MNP-labeled nucleotide precursors and a tunable reference oscillator in accordance with some embodiments.

FIG. 12A illustrates a method 550 suitable for DNA sequencing using MNP-labeled nucleotide precursors and a tunable reference oscillator 610 in accordance with some embodiments. At 552, the method 550 begins. At 554, each nucleotide precursor type (G, A, C, T) is labeled by a different MNP type (e.g., A by MNP1, T by MNP2, C by MNP3, and G by MNP4). At 556, nucleic acid strands to be sequenced, polymerase molecules, and the MNP-labeled nucleotide precursors are introduced in to the fluidic channel 115 of a detection device 100. After a period of time suitable to allow incorporation of the nucleotide precursors, at 558, the frequency of the reference oscillator is swept, and the detection circuit (e.g., circuit 600A) determines the state of each sensor 105 (e.g., some or all of the sensors 105 of the detection device 100). At 560, each sensor 105's state (e.g., its output signal) is analyzed/processed to identify which of the four MNP types was detected at each of the sensors 105. The identity of the incorporated nucleotide precursor can then be determined, and the identity of the paired base is known and can be recorded. The method 550 ends at 562.

Alternatively, as also explained above (see, e.g., the discussion of FIG. 7B), the detection circuitry 130 may include a plurality of reference oscillators 610, each configured to generate a frequency that is close to the frequency of the STO's RF signal in the presence of one of the MNPs being used. During each sequencing cycle, after the four MNP-labeled nucleotide precursors are introduced, a switch 611 may cycle through each RO 610, and the DC output 620 of the circuit 600B may be detected as described in the discussion of FIG. 7B above. Once again, the DC output 620 should be nonzero only when the switch 611 is connected to the RO 610 that is oscillating at approximately the frequency of the STO. From this information, the identity of the particle can be determined.

Figure 12B:
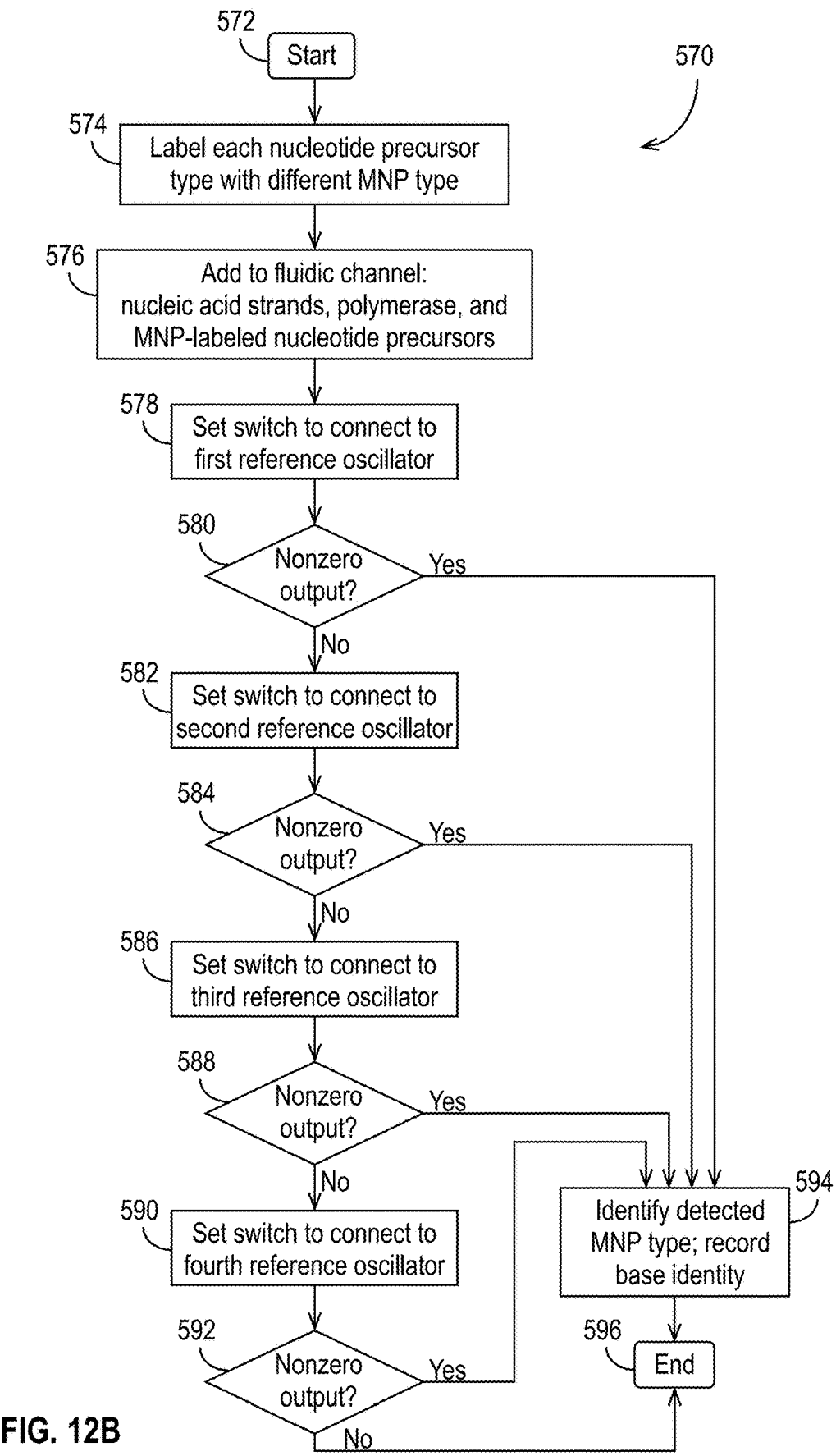
FIG. 12B illustrates a method suitable for DNA sequencing using MNP-labeled nucleotide precursors and a plurality of reference oscillators in accordance with some embodiments.

FIG. 12B illustrates a method 570 suitable for DNA sequencing using MNP-labeled nucleotide precursors and a plurality of reference oscillators 610 in accordance with some embodiments. FIG. 12B assumes there are four MNPs in use and, accordingly, four reference oscillators 610, but it is to be appreciated that there may be more or fewer than four reference oscillators 610. The method 570 begins at 572. At 574, each nucleotide precursor type (G, A, C, T) is labeled by a different MNP type (e.g., A by MNP1, T by MNP2, C by MNP3, and G by MNP4). At 576, nucleic acid strands to be sequenced, polymerase molecules, and the MNP-labeled nucleotide precursors are introduced in to the fluidic channel 115 of a detection device 100. After a period of time suitable to allow incorporation of the nucleotide precursors, at 578, a switch 611 is set to connect to a first reference oscillator 610A (see FIG. 7B). At 580, for each of one or more sensors 105 of a detection device 100, it is determined whether the output of the detection circuit is nonzero or above a threshold. If so, then the detected MNP type is identified, the identity of the paired base may be recorded at 594, and the method 570 ends for that sensor 105 for the sequencing cycle. If the output of the detection circuit is zero or below the threshold, at 582, the switch 611 is set to connect to a second reference oscillator 610B (see FIG. 7B). At 584, it is determined whether the output of the detection circuit is nonzero or above a threshold (which may be the same as or different from the threshold used previously). If so, then the detected MNP type is identified, the identity of the paired base may be recorded at 594, and the method 570 ends for that sensor 105 for the sequencing cycle. If the output of the detection circuit is zero or below the threshold, at 586, the switch 611 is set to connect to a third reference oscillator 610C (see FIG. 7B). At 588, it is determined whether the output of the detection circuit is nonzero or above a threshold (which may be the same as or different from the thresholds used previously). If so, then the detected MNP type is identified, the identity of the paired base may be recorded at 594, and the method 570 ends for that sensor 105 for the sequencing cycle. If the output of the detection circuit is zero or below a threshold, at 590, the switch 611 is set to connect to a fourth reference oscillator 610D (see FIG. 7B). At 592, it is determined whether the output of the detection circuit is nonzero or above a threshold (which may be the same as or different from the thresholds used previously). If so, then the detected MNP type is identified, the identity of the paired base may be recorded at 594, and the method 570 ends for the sequencing cycle. If not, then the method 570 ends at 596.

Methods of Fabricating Sensors and Detection Devices

Figure 13A:
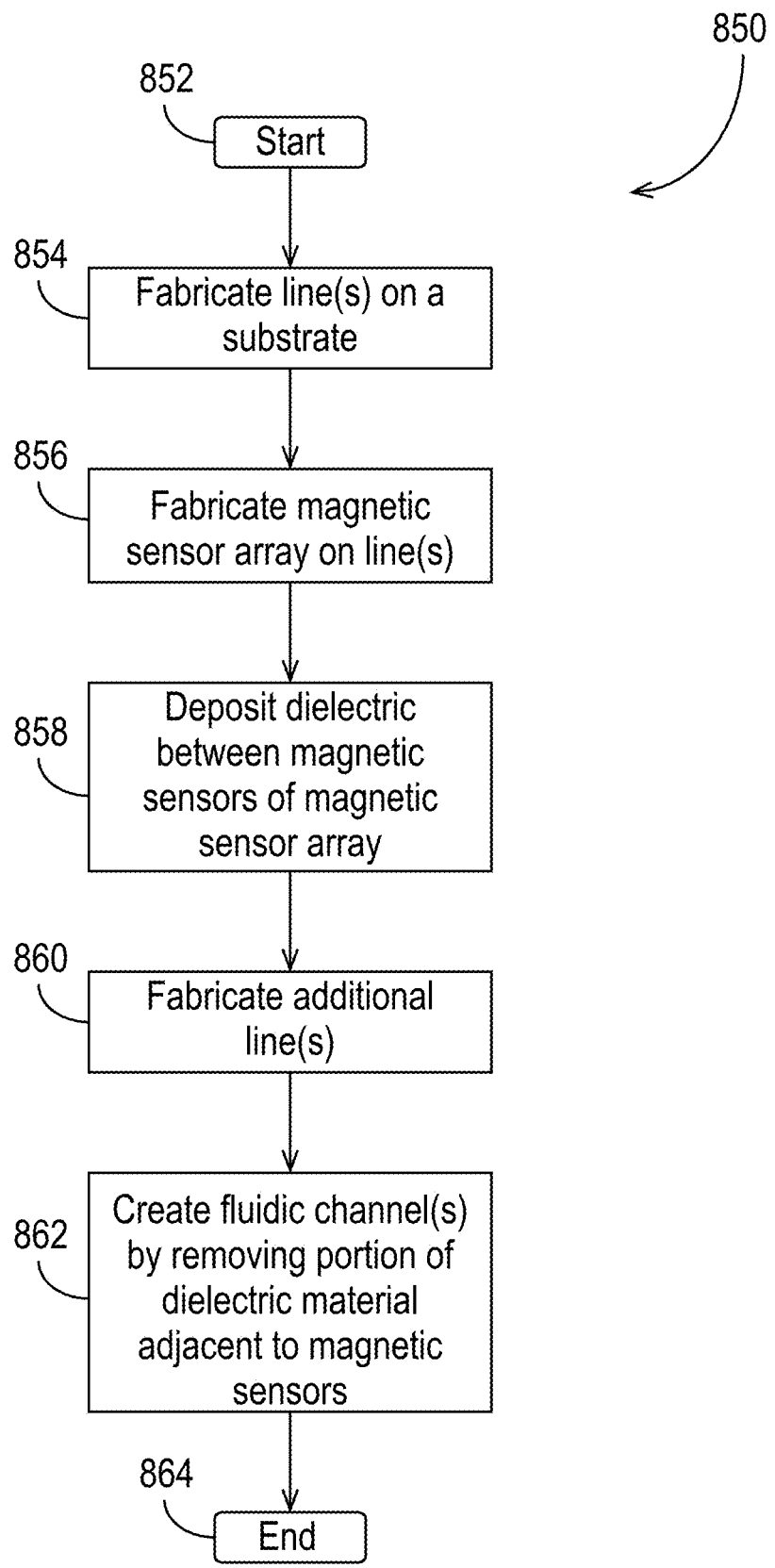
FIG. 13A illustrates a method of manufacturing a detection device in accordance with some embodiments.
Figure 13B:
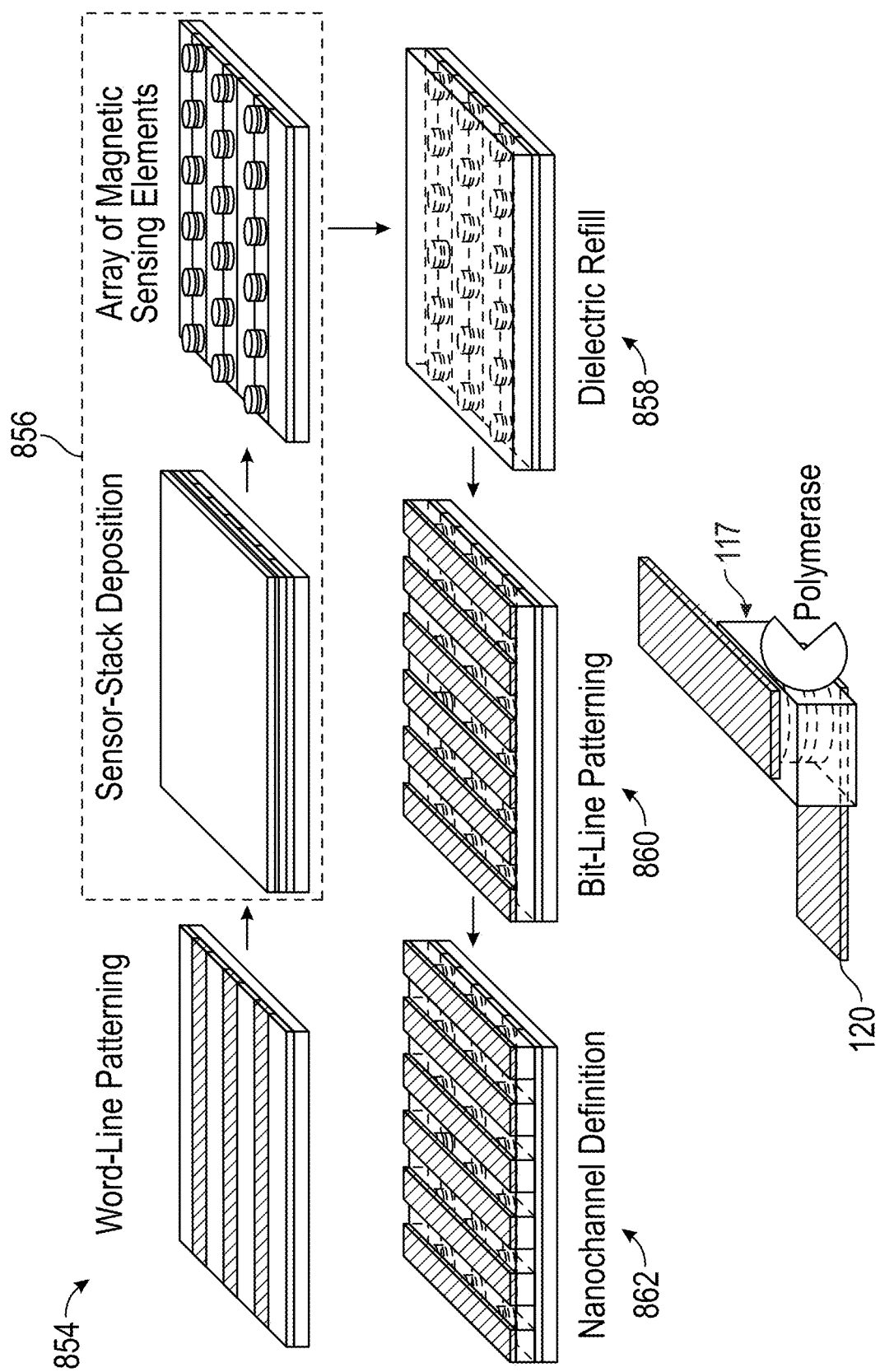
FIG. 13B illustrates the results of each step of the fabrication process of FIG. 13A in accordance with some embodiments.

In some embodiments, the detection device 100 is fabricated using photolithographic processes and thin film deposition. FIG. 13A illustrates a method 850 of manufacturing the detection device 100, and FIG. 13B illustrates the results of steps of the fabrication method 850 with a final panel showing polymerase bound to the wall 117 proximate to a sensor 105 in accordance with some embodiments (e.g., when the detection device 100 is used for nucleic acid sequencing). At 852, the method 850 begins. At 854, at least one line 120 is fabricated on a substrate, for example, by depositing one or more metal layers, using, for example, photolithography to pattern an array of lines and spaces in a polymer layer applied on top of the metal layers, using that polymer layer as a mask for etching the metal layers into an array of lines, depositing an insulating dielectric material, stripping the polymer layer and dielectric material over the lines, and performing chemical mechanical polishing to planarize the surface. At 856, the sensor array 110 is fabricated on the at least one line 120. Each sensor 105 of the sensor array 110 has a bottom portion 108 and a top portion 109. (See FIG. 1A.) The bottom portion 108 is coupled to the at least one line 120. In some embodiments, the bottom portion 108 of each sensor 105 is in contact with the at least one line 120.

At 858, dielectric material is deposited between the sensors 105 of the sensor array 110. At 860, additional lines 120 are fabricated. Each of these additional lines 120 is coupled to the top portion 109 of at least one sensor 105 in the sensor array 110. In some embodiments, the top portion 109 of each sensor 105 is in contact with a line 120. In some embodiments, the bottom portion 108 of a sensor 105 is in contact with a first line 120A, and the top portion 109 of the sensor 105 is in contact with a second line 120B. At 862, a portion of the dielectric material adjacent to the sensors 105 is removed (e.g., by milling, etching, or any other suitable removal process) to create the fluidic channel 115. At 864, the method 850 ends.

Electrical detection for DNA sequencing described in this disclosure may provide a variety of advantages over currently-used technologies involving optical detection methods. For example, electrical detection is not limited in terms of scaling flow cell dimensions in the same manner that optical detection is limited due to optical imaging being diffraction limited. Magnetic detection is a form of electrical detection for sequencing that has advantages over commonly proposed tunnel current detection schemes, because tunneling current methods measure very small currents (which reduces SNR), and the tunnel junction elements are exposed directly to the sequencing chemistries, which could cause corrosion or other detrimental issues that degrade the accuracy of the sequencing process. By comparison, magnetic detection has larger signals (and better SNR) and can be performed without labeling particles being in direct contact with the sensors 105, thereby allowing sensors 105 to be coated in a protective layer that mitigates interactions with the sequencing reagents.

For various embodiments described herein, the STO detection techniques can be used in a relatively simple binary process to detect the presence of an introduced DNA nucleotide precursor (e.g., via detection of a finite or approximately zero voltage at the output of an analog detection circuit). As such, it can reduce the SNR needed to operate the detection system at a high level of accuracy, which makes STO design easier. It also provides flexibility in the choice of MNPs used as labels for the molecules to be detected because only a small magnetic field without any particular field direction turns off or turns on the STO. Thus, both superparamagnetic and ferromagnetic particles may be used without use of an external magnetic field to align particles at different sites in the flow cell (e.g., sensor array 110).

Embodiments herein that use digital processing for detection may also be advantageous to detect STO oscillation frequencies and/or changes in STO oscillation frequencies using reliable, accurate hardware components (e.g., ADCs and DSPs or other similar components) and well-understood algorithms (e.g., Fourier transforms or any other known frequency-analysis techniques to assess the frequency content of the RF signal).

A limitation of magnetic detection may be the SNR of the sensor 105. An advantage of some of the disclosed embodiments is that the STO 604 operates at a higher frequency and will thus have reduced 1/f noise, which results in reduced total noise. Another advantage is that because a single voltage is detected at the output of the detector, use of STOs 604 should be fast and should allow for high data collection throughput, which is desirable in detection systems (e.g., for DNA sequencing).

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

The terms "over," "under," "between," "on," and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The terms "exemplary" and "embodiment" are used to express examples, not preferences or requirements. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrases "at least one of X, Y, and Z," "at least one of X, Y, or Z," "one or more of X, Y, and Z," and "one or more of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The drawings are not necessarily to scale, and the dimensions, shapes, and sizes of the features may differ substantially from how they are depicted in the drawings.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope. Accordingly, the specification and drawings are to be regarded in an illustrative rather than a restrictive sense.

The invention claimed is:

1. A detection device, comprising:
    a sensor comprising a spin torque oscillator (STO);
    at least one fluidic channel configured to receive molecules to be detected, wherein each of a plurality of the molecules to be detected is labeled by at least one magnetic nanoparticle (MNP) of a plurality of MNPs, the plurality of MNPs including at least two distinct groups of MNPs, the at least two distinct groups of MNPs including a first MNP group and a second MNP group; and
    detection circuitry coupled to the sensor and configured to detect presence or absence of magnetization oscillations of the STO in a specified frequency band in response to presence or absence of one or more MNPs coupled to one or more binding sites to be sensed by the sensor, the detection circuitry comprising:
        a first reference oscillator configured to generate a first reference signal at a first frequency, the first frequency being substantially equal to an expected oscillation frequency of the STO in response to presence of one or more MNPs from the first MNP group,
        a second reference oscillator configured to generate a second reference signal at a second frequency, the second frequency being substantially equal to an expected oscillation frequency of the STO in response to presence of one or more MNPs from the second MNP group;
        a mixer; and
        a switch coupled to a first input of the mixer and configured to couple either the first reference oscillator or the second reference oscillator to the first input of the mixer,
    wherein the sensor is encapsulated by a material separating the sensor from the at least one fluidic channel, a surface of the material providing binding sites for the molecules to be detected,
    and wherein a second input of the mixer is coupled to the STO, and wherein the mixer is configured to mix a signal output from the STO with either the first reference signal or the second reference signal to produce an output signal for processing.

2. The detection device of claim 1, wherein the detection circuitry is configured to detect the presence or absence of the magnetization oscillations of the STO in the specified frequency band at least by applying a DC current to the STO.

3. The detection device of claim 2, wherein a magnetization of the STO is configured to (a) oscillate in the specified frequency band in the absence of the one or more MNPs and to fail to oscillate in the specified frequency band in the presence of the one or more MNPs, or (b) oscillate in the specified frequency band in the presence of the one or more MNPs and to fail to oscillate in the specified frequency band in the absence of the one or more MNPs.

4. The detection device of claim 2, wherein a magnetization of the STO is configured to (a) oscillate in the specified frequency band in the absence of the one or more MNPs and oscillate in a different frequency band in the presence of the one or more MNPs, the different frequency band being disjoint from the specified frequency band, or (b) oscillate in the specified frequency band in the presence of the one or more MNPs and oscillate in the different frequency band in the absence of the one or more MNPs.

5. The detection device of claim 2, wherein at least one MNP of the plurality of MNPs is superparamagnetic or ferromagnetic.

6. The detection device of claim 1, wherein the first frequency of the first reference signal is selectable, and wherein the detection circuitry is further configured to select the first frequency of the first reference signal to substantially match the expected oscillation frequency of the STO in response to the presence of the one or more MNPs from the first MNP group.

7. The detection device of claim 1, wherein the second frequency of the second reference signal is selectable, and wherein the detection circuitry is further configured to select the second frequency of the second reference signal to substantially match the expected oscillation frequency of the STO in response to the presence of the one or more MNPs from the second MNP group.

8. The detection device of claim 1, wherein the detection circuitry
further comprises:
a radio-frequency (RF) amplifier;
a filter coupled to and disposed between the STO and an input of the RF amplifier; and
a diode or envelope detector coupled to an output of the mixer,
wherein:
the RF amplifier is coupled to and disposed between an output of the filter and an input to the mixer.

9. The detection device of claim 8, wherein the filter is a high-pass filter or a band-pass filter.

10. The detection device of claim 8, wherein the filter is a first filter, and wherein
the detection circuitry further comprises:
a second filter coupled to the output of the mixer; and
an additional amplifier coupled to and disposed between an output of the second filter and an input of the diode or envelope detector.

11. The detection device of claim 10, wherein the second filter is a low-pass filter or a band-pass filter.

12. The detection device of claim 1, wherein the STO comprises a pinned layer, a free layer, and a spacer layer disposed between the pinned layer and the free layer.

13. The detection device of claim 12, wherein, in a quiescent state of magnetization, a magnetic moment of the free layer is (a) oriented substantially co-linearly with a magnetic moment of the pinned layer, (b) oriented substantially parallel to or anti-parallel to the magnetic moment of the pinned layer, or (c) oriented at an angle to the magnetic moment of the pinned layer, wherein the angle is between approximately 20 degrees and approximately 60 degrees.

14. A detection device, comprising:
a sensor comprising a spin torque oscillator (STO);
at least one fluidic channel configured to receive molecules to be detected, wherein each of a plurality of the molecules to be detected is labeled by at least one magnetic nanoparticle (MNP) of a plurality of MNPs, the plurality of MNPs including at least two distinct groups of MNPs, the at least two distinct groups of MNPs including a first MNP group and a second MNP group; and
detection circuitry coupled to the sensor and configured to detect presence or absence of magnetization oscillations of the STO in a specified frequency band in response to presence or absence of one or more MNPs coupled to one or more binding sites to be sensed by the sensor, wherein the detection circuitry comprises:
a reference oscillator coupled to the STO;
a processor;
an analog-to-digital converter (ADC) coupled to an input of the processor; and
a low-pass or band-pass filter coupled to an input of the ADC and configured to filter a signal output from the STO and the reference oscillator to generate a signal to be processed by the ADC and the processor.

15. The detection device of claim 14, wherein the sensor is a first sensor
and the STO is a first STO, and further comprising:
a second sensor comprising a second STO,
wherein:
the second sensor is encapsulated by material separating the second sensor from the at least one fluidic channel,
the detection circuitry is further configured to detect presence or absence of magnetization oscillations of the second STO in the specified frequency band in response to presence of absence of at least one MNP coupled to one or more binding sites associated with the second sensor, and
the reference oscillator is also coupled to the second STO.

16. The detection device of claim 14, wherein the detection circuitry is configured to detect the presence or absence of the magnetization oscillations of the STO in the specified frequency band at least by applying a DC current to the STO.

17. The detection device of claim 16, wherein a magnetization of the STO is configured to (a) oscillate in the specified frequency band in the absence of the one or more MNPs and to fail to oscillate in the specified frequency band in the presence of the one or more MNPs, or (b) oscillate in the specified frequency band in the presence of the one or more MNPs and to fail to oscillate in the specified frequency band in the absence of the one or more MNPs.

18. The detection device of claim 16, wherein a magnetization of the STO is configured to (a) oscillate in the specified frequency band in the absence of the one or more MNPs and oscillate in a different frequency band in the presence of the one or more MNPs, the different frequency band being disjoint from the specified frequency band, or (b) oscillate in the specified frequency band in the presence of the one or more MNPs and oscillate in the different frequency band in the absence of the one or more MNPs.

19. The detection device of claim 16, wherein at least one MNP of the plurality of MNPs is superparamagnetic or ferromagnetic.

20. The detection device of claim 14, wherein the STO comprises a pinned layer, a free layer, and a spacer layer disposed between the pinned layer and the free layer.

21. The detection device of claim 20, wherein, in a quiescent state of magnetization, a magnetic moment of the free layer is (a) oriented substantially co-linearly with a magnetic moment of the pinned layer, (b) oriented substantially parallel to or anti-parallel to the magnetic moment of the pinned layer, or (c) oriented at an angle to the magnetic moment of the pinned layer, wherein the angle is between approximately 20 degrees and approximately 60 degrees.

22. The detection device of claim 14, wherein the reference oscillator is configured to generate a reference signal, wherein a frequency of the reference signal is selectable, and wherein the detection circuitry is further configured to select the frequency of the reference signal to substantially match (a) an expected oscillation frequency of the STO in the presence of the one or more MNPs, or (b) an expected oscillation frequency of the STO in the absence of the one or more MNPs.

23. A detection device, comprising:
a sensor comprising a spin torque oscillator (STO);
at least one fluidic channel configured to receive molecules to be detected, wherein each of a plurality of the molecules to be detected is labeled by at least one magnetic nanoparticle (MNP) of a plurality of MNPs, the plurality of MNPs including at least two distinct groups of MNPs, the at least two distinct groups of MNPs including a first MNP group and a second MNP group; and detection circuitry coupled to the sensor and configured to detect presence or absence of magnetization oscillations of the STO in a specified frequency band in response to presence or absence of one or more MNPs coupled to one or more binding sites to be sensed by the sensor, wherein the detection circuitry comprises:
a direct radio-frequency (RF) analog-to-digital converter (ADC);
a processor coupled to an output of the direct RF ADC; and
a high-pass or band-pass filter disposed between and coupled to the STO and an input of the direct RF ADC.

24. The detection device of claim 23, wherein the detection circuitry is configured to detect the presence or absence of the magnetization oscillations of the STO in the specified frequency band at least by applying a DC current to the STO.

25. The detection device of claim 24, wherein a magnetization of the STO is configured to (a) oscillate in the specified frequency band in the absence of the one or more MNPs and to fail to oscillate in the specified frequency band in the presence of the one or more MNPs, or (b) oscillate in the specified frequency band in the presence of the one or more MNPs and to fail to oscillate in the specified frequency band in the absence of the one or more MNPs.

26. The detection device of claim 24, wherein a magnetization of the STO is configured to (a) oscillate in the specified frequency band in the absence of the one or more MNPs and oscillate in a different frequency band in the presence of the one or more MNPs, the different frequency band being disjoint from the specified frequency band, or (b) oscillate in the specified frequency band in the presence of the one or more MNPs and oscillate in the different frequency band in the absence of the one or more MNPs.

27. The detection device of claim 24, wherein at least one MNP of the plurality of MNPs is superparamagnetic or ferromagnetic.

28. The detection device of claim 23, wherein the STO comprises a pinned layer, a free layer, and a spacer layer disposed between the pinned layer and the free layer.

29. The detection device of claim 28, wherein, in a quiescent state of magnetization, a magnetic moment of the free layer is (a) oriented substantially co-linearly with a magnetic moment of the pinned layer, (b) oriented substantially parallel to or anti-parallel to the magnetic moment of the pinned layer, or (c) oriented at an angle to the magnetic moment of the pinned layer, wherein the angle is between approximately 20 degrees and approximately 60 degrees.

30. A detection device, comprising:
a sensor comprising a spin torque oscillator (STO);
at least one fluidic channel configured to receive molecules to be detected, wherein each of a plurality of the molecules to be detected is labeled by at least one magnetic nanoparticle (MNP) of a plurality of MNPs, the plurality of MNPs including at least two distinct groups of MNPs, the at least two distinct groups of MNPs including a first MNP group and a second MNP group; and
detection circuitry coupled to the sensor and configured to detect presence or absence of magnetization oscillations of the STO in a specified frequency band in response to presence or absence of one or more MNPs coupled to one or more binding sites to be sensed by the sensor, wherein the detection circuitry comprises:
a processor; and
an analog-to-digital converter (ADC) disposed between the STO and the processor and configured to provide samples of a signal generated by the STO to the processor,
and wherein the processor is programmed to execute machine-executable instructions that cause the processor to perform a frequency-domain analysis of the samples to detect the presence or absence of magnetization oscillations of the STO in the specified frequency band.

31. The detection device of claim 30, wherein the detection circuitry is configured to detect the presence or absence of the magnetization oscillations of the STO in the specified frequency band at least by applying a DC current to the STO.

32. The detection device of claim 31, wherein a magnetization of the STO is configured to (a) oscillate in the specified frequency band in the absence of the one or more MNPs and to fail to oscillate in the specified frequency band in the presence of the one or more MNPs, or (b) oscillate in the specified frequency band in the presence of the one or more MNPs and to fail to oscillate in the specified frequency band in the absence of the one or more MNPs.

33. The detection device of claim 31, wherein a magnetization of the STO is configured to (a) oscillate in the specified frequency band in the absence of the one or more MNPs and oscillate in a different frequency band in the presence of the one or more MNPs, the different frequency band being disjoint from the specified frequency band, or (b) oscillate in the specified frequency band in the presence of the one or more MNPs and oscillate in the different frequency band in the absence of the one or more MNPs.

34. The detection device of claim 31, wherein at least one MNP of the plurality of MNPs is superparamagnetic or ferromagnetic.

35. The detection device of claim 30, wherein performing a frequency-domain analysis of the samples to detect the presence or absence of magnetization oscillations of the STO in the specified frequency band comprises applying a Fourier transform to the samples.

36. The detection device of claim 30, wherein the STO comprises a pinned layer, a free layer, and a spacer layer disposed between the pinned layer and the free layer.

37. The detection device of claim 36, wherein, in a quiescent state of magnetization, a magnetic moment of the free layer is (a) oriented substantially co-linearly with a magnetic moment of the pinned layer, (b) oriented substantially parallel to or anti-parallel to the magnetic moment of the pinned layer, or (c) oriented at an angle to the magnetic moment of the pinned layer, wherein the angle is between approximately 20 degrees and approximately 60 degrees.

38. A detection device, comprising:
a sensor comprising a spin torque oscillator (STO);
at least one fluidic channel configured to receive molecules to be detected, wherein each of a plurality of the molecules to be detected is labeled by at least one magnetic nanoparticle (MNP) of a plurality of MNPs, the plurality of MNPs including at least two distinct groups of MNPs, the at least two distinct groups of MNPs including a first MNP group and a second MNP group; and
detection circuitry coupled to the sensor and configured to detect presence or absence of magnetization oscillations of the STO in a specified frequency band in response to presence or absence of one or more MNPs coupled to one or more binding sites to be sensed by the sensor, wherein the detection circuitry comprises:
an amplifier coupled to the STO;
an analog-to-digital converter (ADC) coupled to an output of the amplifier; and
a processor coupled to an output of the ADC.

39. The detection device of claim 38, wherein the processor is a digital signal processor (DSP).

40. The detection device of claim 38, wherein the processor is programmed to execute machine-executable instructions that cause the processor to identify the presence of the magnetization oscillations of the STO within the specified frequency band.

41. The detection device of claim 38, wherein the processor is programmed to execute machine-executable instructions that cause the processor to:
receive, from the ADC, samples of a signal generated by the STO,
apply a Fourier transform to the samples, and
determine whether a result of the Fourier transform indicates the presence or absence of magnetization oscillations of the STO in the specified frequency band to detect the presence or absence of magnetization oscillations of the STO in the specified frequency band.

42. The detection device of claim 38, wherein the detection circuitry further comprises one or more of:
(a) a high-pass filter disposed between the STO and the amplifier;
(b) a band-pass filter disposed between the STO and the amplifier;
(c) a mixer having first and second inputs and an output, the first input being coupled to the output of the amplifier, the second input being coupled to an output of a reference oscillator, and the output of the mixer being coupled to an input of the ADC;
(d) a low-pass filter disposed between the output of the amplifier and the input of the ADC; or
(e) a band-pass filter disposed between the output of the amplifier and the input of the ADC.

43. The detection device of claim 38, wherein the detection circuitry is configured to detect the presence or absence of the magnetization oscillations of the STO in the specified frequency band at least by applying a DC current to the STO.

44. The detection device of claim 43, wherein a magnetization of the STO is configured to (a) oscillate in the specified frequency band in the absence of the one or more MNPs and to fail to oscillate in the specified frequency band in the presence of the one or more MNPs, or (b) oscillate in the specified frequency band in the presence of the one or more MNPs and to fail to oscillate in the specified frequency band in the absence of the one or more MNPs.

45. The detection device of claim 43, wherein a magnetization of the STO is configured to (a) oscillate in the specified frequency band in the absence of the one or more MNPs and oscillate in a different frequency band in the presence of the one or more MNPs, the different frequency band being disjoint from the specified frequency band, or (b) oscillate in the specified frequency band in the presence of the one or more MNPs and oscillate in the different frequency band in the absence of the one or more MNPs.

46. The detection device of claim 43, wherein at least one MNP of the plurality of MNPs is superparamagnetic or ferromagnetic.

47. The detection device of claim 38, wherein the STO comprises a pinned layer, a free layer, and a spacer layer disposed between the pinned layer and the free layer.

48. The detection device of claim 47, wherein, in a quiescent state of magnetization, a magnetic moment of the free layer is (a) oriented substantially co-linearly with a magnetic moment of the pinned layer, (b) oriented substantially parallel to or anti-parallel to the magnetic moment of the pinned layer, or (c) oriented at an angle to the magnetic moment of the pinned layer, wherein the angle is between approximately 20 degrees and approximately 60 degrees.

* * * * *